United States Patent
Brown et al.

(10) Patent No.: US 10,259,802 B2
(45) Date of Patent: *Apr. 16, 2019

(54) BICYCLIC AZA COMPOUNDS AS MUSCARINIC M1 RECEPTOR ANTAGONISTS

(71) Applicant: Heptares Therapeutics Limited, Welwyn Garden (GB)

(72) Inventors: Giles Albert Brown, Welwyn Garden (GB); Julie Elaine Cansfield, Welwyn Garden (GB); Miles Stuart Congreve, Welwyn Garden (GB); Mark Pickworth, Welwyn Garden (GB); Benjamin Gerald Tehan, Welwyn Garden (GB)

(73) Assignee: Heptares Therapeutics Limited, Welwyn Garden City (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,278

(22) Filed: May 15, 2018

(65) Prior Publication Data

US 2018/0258085 A1 Sep. 13, 2018

Related U.S. Application Data

(63) Continuation of application No. 15/595,107, filed on May 15, 2017, now Pat. No. 9,975,890, which is a continuation of application No. 14/996,829, filed on Jan. 15, 2016, now Pat. No. 9,669,013, which is a continuation of application No. 14/428,927, filed as application No. PCT/GB2013/052442 on Sep. 18, 2013, now Pat. No. 9,266,857.

(60) Provisional application No. 61/823,606, filed on May 15, 2013, provisional application No. 61/702,330, filed on Sep. 18, 2012.

(51) Int. Cl.
| | |
|---|---|
| C07D 211/06 | (2006.01) |
| C07D 295/00 | (2006.01) |
| C07D 401/04 | (2006.01) |
| C07D 401/08 | (2006.01) |
| C07D 451/04 | (2006.01) |
| C07B 59/00 | (2006.01) |
| A61K 31/439 | (2006.01) |
| A61K 31/4439 | (2006.01) |

(52) U.S. Cl.
CPC ......... *C07D 401/04* (2013.01); *A61K 31/439* (2013.01); *A61K 31/4439* (2013.01); *C07B 59/002* (2013.01); *C07D 401/08* (2013.01); *C07D 451/04* (2013.01); *C07B 2200/05* (2013.01)

(58) Field of Classification Search
CPC ... C07D 211/06; C07D 295/00; C07D 401/04
USPC ....................................................... 546/184
See application file for complete search history.

(56) References Cited

U.S. PATENT DOCUMENTS

| | | | |
|---|---|---|---|
| 7,524,852 B2 | 4/2009 | Arai et al. | |
| 9,266,857 B2 * | 2/2016 | Brown | C07D 401/04 |
| 9,669,013 B2 | 6/2017 | Brown et al. | |
| 9,975,890 B2 * | 5/2018 | Brown | C07D 401/04 |
| 2007/0054911 A1 | 3/2007 | Drutu et al. | |

FOREIGN PATENT DOCUMENTS

| | | |
|---|---|---|
| CN | 101501024 A | 8/2009 |
| WO | 1999/32479 A1 | 7/1999 |
| WO | 2007/076070 A2 | 7/2007 |
| WO | 2009/034380 A1 | 3/2009 |
| WO | 2011112825 A2 | 9/2011 |
| WO | 2013/072705 A1 | 5/2013 |

OTHER PUBLICATIONS

Foster et al., Neuropsychiatric disease and treatment (10) 183-191, 2014.

* cited by examiner

*Primary Examiner* — Niloofar Rahmani
(74) *Attorney, Agent, or Firm* — McCarter & English, LLP; Steven G. Davis; Mei Bai

(57) ABSTRACT

This invention relates to compounds (Formula (1)) that are agonists of the muscarinic M1 receptor and which are useful in the treatment of muscarinic M1 receptor mediated diseases. Also provided are pharmaceutical compositions containing the compounds and the therapeutic uses of the compounds. Compounds provided are of formula where $R_1$-$R_5$, $X_1$, $X_2$ and p are as defined herein.

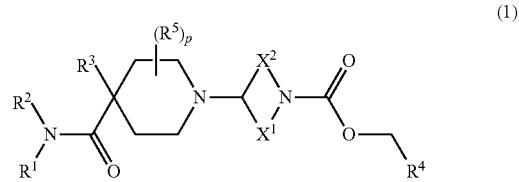

(1)

20 Claims, 1 Drawing Sheet

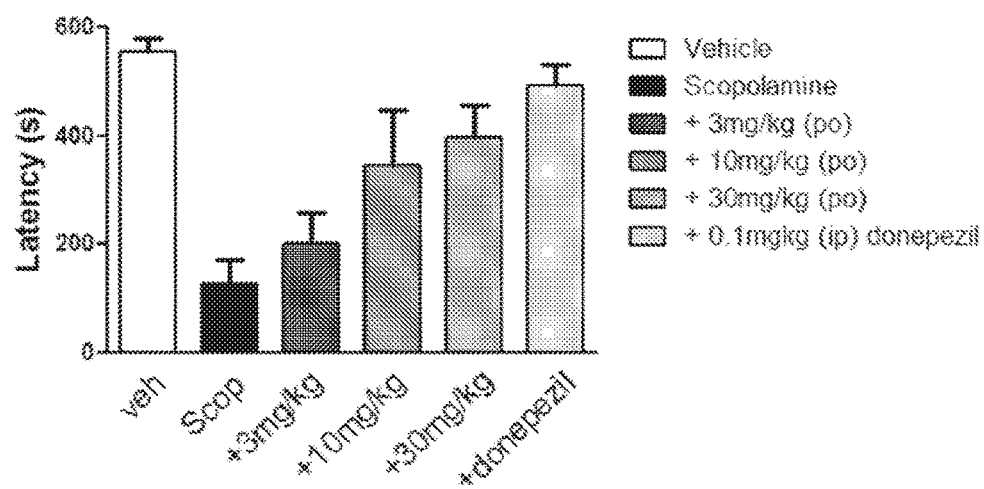

BICYCLIC AZA COMPOUNDS AS MUSCARINIC M1 RECEPTOR ANTAGONISTS

RELATED APPLICATION INFORMATION

This application is a continuation of U.S. patent application Ser. No.: 15/595,107, filed May 15, 2017, now U.S. Patent No.: 9,975,890, which is a continuation of U.S. patent application Ser. No.: 14/996,829, filed Jan. 15, 2016, now U.S. Patent No.: 9,669,013, which is a continuation of U.S. patent application Ser. No.: 14/428,927, filed Mar. 17, 2015, now U.S. Patent No.: 9,266,857, which is a 371 national stage of International Patent Application PCT/GB2013/052442, filed Sep. 18, 2013, which claims the benefit of U.S. Provisional Application Serial No: 61/823,606, filed May 15, 2013, and of U.S. Provisional Application Serial No.: 61/702,330, filed Sep. 18, 2012. The entire contents of these applications are incorporated herein by reference in their entirety.

This invention relates to a class of novel amide compounds, their salts, pharmaceutical compositions containing them and their use in therapy of the human body. In particular, the invention is directed to a class of amide compounds, which are muscarinic M1 receptor agonists, and hence are useful in the treatment of Alzheimer's Disease, schizophrenia, cognitive disorders and other diseases mediated by the muscarinic M1 receptor, as well as the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al. 1982 *Science*). In schizophrenia, which is also characterised by cognitive impairments, mAChR density is reduced in the pre-frontal cortex, hippocampus and caudate putamen of schizophrenic subjects (Dean et al., 2002 *Mol Psychiatry*). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (http://www.drugs.com/pro/donepezil.html; http://www.drugs.com/pro/rivastigmine.html).

Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidgenic and amyloidgenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 *Neuron*). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*).

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic side effects, including nausea, gastrointestinal pain, diarrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/ traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the M1 receptor in pain is reviewed by D. F. Fiorino and M. Garcia-Guzman, 2012.

Recently, a small number of compounds have been identified which display improved selectivity for the $M_1$ mAChR subtype over the peripherally expressed mAChR subtypes (Bridges et al., 2008 Bioorg Med Chem Lett; Johnson et al., 2010 Bioorg Med Chem Lett; Budzik et al., 2010 ACS Med Chem Lett). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ mAChR over the $M_2$ and $M_3$ receptor subtypes.

FIGURES

Compounds of the invention reduce scopolamine-induced amnesia in a dose-dependent manner.

FIG. 1 shows that Example 9 Isomer 2 was found to reverse scopolamine-induced amnesia of the paradigm in a dose-dependent manner, with an approximate ED50 of ca. 10 mg/kg (po). The effect of 30 mg/kg was similar to that produced by the cholinesterase inhibitor donepezil (0.1 mg/kg, ip) which served as a positive control.

THE INVENTION

The present invention provides compounds having activity as muscarnic M1 receptor agonists. More particularly, the invention provides compounds that exhibit selectivity for the M1 receptor relative to the M2 and M3 receptor subtypes.

Accordingly, in a first embodiment (Embodiment 1.1), the invention provides a compound of the formula (1):

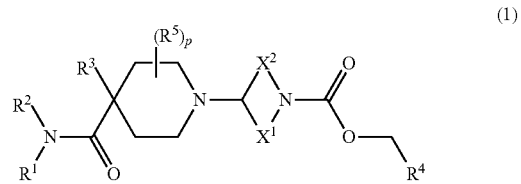

or a salt thereof, wherein:

p is 0, 1 or 2;

$X^1$ and $X^2$ are saturated hydrocarbon groups which together contain a total of five to nine carbon atoms and which link together such that the moiety:

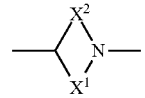

forms a bicyclic ring system;

$R^1$ is a $C_{1-10}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^2$ is hydrogen or a $C_{1-10}$ non-aromatic hydrocarbon group;

or $R^1$ and $R^2$ together with the nitrogen atom to which they are attached form a non-aromatic heterocyclic ring of four to nine ring members, wherein the heterocyclic ring may optionally contain a second heteroatom selected from O, N and S and oxidised forms thereof; and wherein the heterocyclic ring may optionally be substituted with one to six substituents selected from $C_{1-2}$ alkyl; fluorine; and cyano;

$R^3$ is selected from hydrogen; halogen; cyano; hydroxy; $C_{1-3}$ alkoxy; and a $C_{1-5}$ non-aromatic hydrocarbon group which is optionally substituted with one to six fluorine atoms and wherein one or two, but not all, carbon atoms of the hydrocarbon group may optionally be replaced by a heteroatom selected from O, N and S;

$R^4$ is a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof; and $R^5$ is fluorine.

Particular and preferred compounds of the formula (1) are as defined in the following Embodiments 1.2 to 1.64:

1.2 A compound according to Embodiment 1.1 wherein $R^1$ is a $C_{1-10}$ non-aromatic hydrocarbon group containing 0, 1 or 2 carbon-carbon multiple bonds, wherein the hydrocarbon group is optionally substituted with one to six fluorine atoms and wherein one or two, but not all, carbon atoms of the hydrocarbon group may optionally be replaced by a heteroatom selected from O, N and S and oxidised forms thereof.

1.3 A compound according to either of Embodiments 1.1 and 1.2 wherein $R^1$ is selected from $C_{1-6}$ alkyl; $C_{2-6}$ alkenyl; $C_{2-6}$ alkynyl; and $C_{1-10}$ non-aromatic hydrocarbon groups consisting of or containing a $C_{3-10}$ cycloalkyl or $C_{5-6}$ cycloalkenyl group; each of the said alkyl, alkenyl, alkynyl and non-aromatic hydrocarbon groups being optionally substituted with one to six fluorine atoms and wherein one or two, but not all, carbon atoms of each of the alkyl, alkenyl, alkynyl and non-aromatic hydrocarbon groups may optionally be replaced by a heteroatom selected from O, N and S and oxidised forms thereof.

1.4 A compound according to any one of Embodiments 1.1 to 1.3 wherein $R^1$ is selected from:
  $C_{1-6}$ alkyl optionally substituted with 1 to 6 fluorine atoms;
  methoxy-$C_{1-4}$ alkyl optionally substituted with 1 to 6 fluorine atoms;
  $C_{1-6}$ alkoxy;
  $C_{2-6}$ alkenyl;
  $C_{2-6}$ alkynyl;
  $C_{3-6}$ cycloalkyl optionally substituted with one or two methyl groups;
  $C_{4-5}$ cycloalkyl-$CH_2$— wherein the $C_{4-5}$ cycloalkyl moiety is optionally substituted with one $C_{1-2}$ alkyl group and wherein one carbon atom of the $C_{4-5}$ cycloalkyl moiety may optionally be replaced by an oxygen atom;
  cyclopropyl-$C_{1-3}$ alkyl;
  cyclopentenyl; and
  methyl-bicyclo[2.2.2]octanyl.

1.5 A compound according to Embodiment 1.4 wherein $R^1$ is selected from:
  $C_{1-5}$ alkyl optionally substituted with 1 to 6 fluorine atoms;
  $C_{3-6}$ cycloalkyl optionally substituted with one or two methyl groups;
  $C_{4-5}$ cycloalkyl-$CH_2$— wherein the $C_{4-5}$ cycloalkyl moiety is optionally substituted with one $C_{1-2}$ alkyl group and wherein one carbon atom of the $C_{4-5}$ cycloalkyl moiety may optionally be replaced by an oxygen atom;
  cyclopropyl-$C_{1-3}$ alkyl; and
  methyl-bicyclo[2.2.2]octanyl.

1.6 A compound according to Embodiment 1.5 wherein $R^1$ is $C_{1-5}$ alkyl optionally substituted with 1 to 6 fluorine atoms.

1.7 A compound according to Embodiment 1.5 wherein $R^1$ is $C_{3-6}$ cycloalkyl optionally substituted with one or two methyl groups.

1.8 A compound according to Embodiment 1.5 wherein $R^1$ is $C_{4-5}$ cycloalkyl-$CH_2$— wherein the $C_{4-5}$ cycloalkyl moiety is optionally substituted with one $C_{1-2}$ alkyl group and wherein one carbon atom of the $C_{4-5}$ cycloalkyl moiety may optionally be replaced by an oxygen atom.

1.9 A compound according to Embodiment 1.5 wherein $R^1$ is cyclopropyl-$C_{1-3}$ alkyl.

1.10 A compound according to Embodiment 1.5 wherein $R^1$ is methyl-bicyclo[2.2.2]octanyl.

1.11 A compound according to Embodiment 1.4 wherein $R^1$ is selected from groups A to AH below:

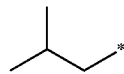

A

B

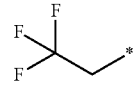

C

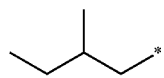

D

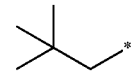

E

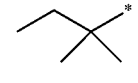

F

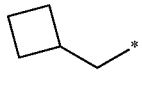

G

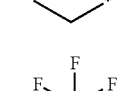

H

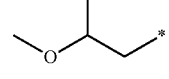

I

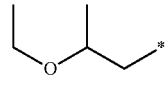

J

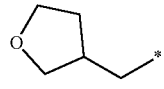

K

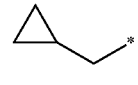

L

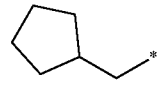

M

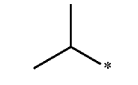

N

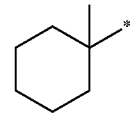

O

P

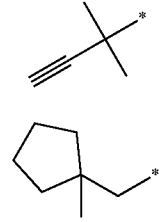

Q

-continued

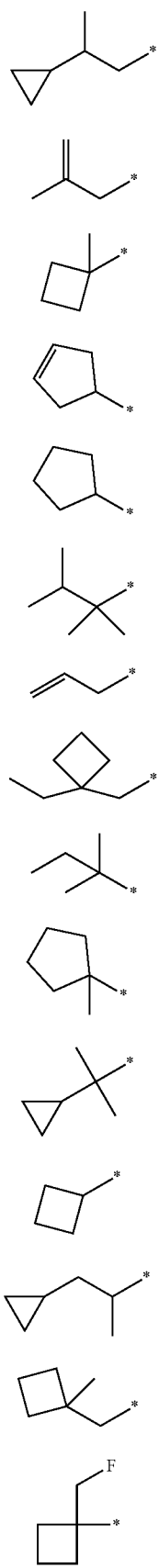

R

S

T

U

V

W

X

Y

Z

AA

AB

AC

AD

AE

AF

-continued

AG

AH where the asterisk denotes the point of attachment of the group to the amide nitrogen atom.

1.12 A compound according to Embodiment 1.11 wherein $R^1$ is selected from groups A, B, D, E, F, G, L, M, N, O, Q, R, T, V, W, Y, AB, AE, AF, AG and AH.

1.13 A compound according to any one of Embodiments 1.1 to 1.4 wherein $R^1$ is selected from 2-methylpropyl; 2,2-dimethylpropyl; tert-butyl; 2-methyl-but-2-yl; 2,3-dimethylbut-2-yl; cyclopropylmethyl; cyclobutylmethyl; cyclopentyl; cyclopentylmethyl; 1-methylcyclobutyl; 1-methylcyclopentyl; 1-methylcyclohexyl; 1-methylcyclopentylmethyl; cyclopropyl-prop-2-yl; 1-methylcyclobutylmethyl, 1-ethyl-cyclobutylmethyl, 1-(fluoromethyl)cyclobutyl, 1-(1,1,1-trideuteromethyl) cyclobutyl and 1-(1,1,1-trideuteromethyl)-2,2,3,3,4,4-hexadeuterocyclobutyl groups.

1.14 A compound according to Embodiment 1.13 wherein $R^1$ is selected from 2-methylpropyl and 1-methylcyclobutyl.

1.15 A compound according to Embodiment 1.14 wherein $R^1$ is 2-methylpropyl.

1.16 A compound according to Embodiment 1.14 wherein $R^1$ is 1-methylcyclobutyl.

1.17 A compound according to any one of Embodiments 1.1 to 1.16 wherein $R^2$ is selected from hydrogen and $C_{1-6}$ alkyl.

1.18 A compound according to Embodiment 1.17 wherein $R^2$ is selected from hydrogen, methyl, ethyl and isopropyl.

1.19 A compound according to Embodiment 1.18 wherein $R^2$ is hydrogen.

1.20 A compound according to any one of Embodiments 1.1 to 1.19 wherein $R^3$ is selected from hydrogen, halogen, cyano, hydroxy, $C_{1-3}$ alkoxy and $C_{1-4}$ alkyl.

1.21 A compound according to Embodiment 1.20 wherein $R^3$ is selected from hydrogen, fluorine, methyl and methoxy.

1.22 A compound according to Embodiment 1.21 wherein $R^3$ is selected from hydrogen, fluorine and methoxy.

1.23 A compound according to Embodiment 1.22 wherein $R^3$ is selected from hydrogen and fluorine.

1.24 A compound according to Embodiment 1.23 wherein $R^3$ is hydrogen.

1.25 A compound according to Embodiment 1.23 wherein $R^3$ is fluorine.

1.26 A compound according to any one of Embodiments 1.1 to 1.25 wherein $R^4$ is an acyclic $C_{1-6}$ hydrocarbon group.

1.27 A compound according to Embodiment 1.26 wherein $R^4$ is an acyclic $C_{1-3}$ hydrocarbon group.

1.28 A compound according to Embodiment 1.27 wherein $R^4$ is a $C_{1-3}$ alkyl group or a $C_{2-3}$ alkynyl group.

1.29 A compound according to Embodiment 1.28 wherein $R^1$ is selected from methyl, ethyl, ethynyl and 1-propynyl.

1.30 A compound according to Embodiment 1.29 wherein $R^1$ is methyl.

1.31 A compound according to any one of Embodiments 1.1 to 1.30 wherein p is 0 or 1.

1.32 A compound according to Embodiment 1.31 wherein p is 0.

1.33 A compound according to Embodiment 1.31 wherein p is 1.

1.34 A compound according to any one of Embodiments 1.1 to 1.33 wherein $X^1$ and $X^2$ together contain six or seven carbon atoms.

1.35 A compound according to any one of Embodiments 1.1 to 1.34 wherein the bicyclic ring system formed by the moiety:

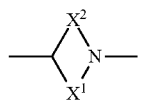

is a bridged bicyclic ring system.

1.36 A compound according to Embodiment 1.35 wherein the bridged bicyclic ring system is an azabicyclo-octane or azabicyclo-nonane ring system.

1.37 A compound according to Embodiment 1.36 wherein the bridged bicyclic ring system is selected from an 8-aza-bicyclo[3.2.1]octane ring system, a 9-aza-bicyclo[3.3.1]nonane ring system and a 6-aza-bicyclo[3.2.1]octane ring system.

1.38 A compound according to Embodiment 1.37 wherein the bridged bicyclic ring system is selected from ring systems BA, BB and BC below:

BA

BB

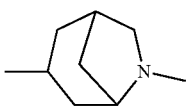
BC 1.39 A compound according to Embodiment 1.38 wherein the bridged bicyclic ring system is ring system BA.

1.40 A compound according to Embodiment 1.38 wherein the bridged bicyclic ring system is ring system BB.

1.41 A compound according to Embodiment 1.38 wherein the bridged bicyclic ring system is ring system BC.

1.42 A compound according to any one of Embodiments 1.1 to 1.34 wherein the bicyclic ring system formed by the moiety:

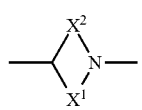

is a spirocyclic ring system.

1.43 A compound according to Embodiment 1.42 wherein the spirocyclic ring system is a 2-aza-spiro[3.4]octane or a 6-aza-spiro[3.4]octane ring system.

1.44 A compound according to Embodiment 1.43 wherein the spirocyclic ring system is selected from ring systems CA and CB below:

CA

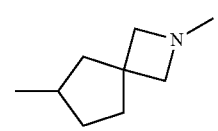
CB 1.45 A compound according to Embodiment 1.44 wherein the spirocyclic ring system is ring system CA.

1.46 A compound according to Embodiment 1.44 wherein the spirocyclic ring system is ring system CB.

1.47 A compound according to any one of Embodiments 1.1 to 1.34 wherein the bicyclic ring system formed by the moiety:

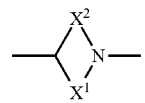

is a fused bicyclic ring system.

1.48 A compound according to Embodiment 1.47 wherein the fused bicyclic ring system is a cyclopentanopyrrolidine ring system.

1.49 A compound according to Embodiment 1.47 wherein the cyclopentanopyrrolidine ring system has structure DA below

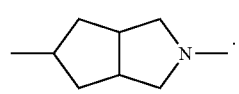
DA 1.50 A compound according to any one of Embodiments 1.1 to 1.34 wherein the bicyclic ring system formed by the moiety:

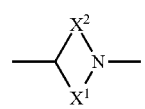

is selected from:

(a) an azabicyclo-octane or azabicyclo-nonane ring system;

(b) a 2-aza-spiro[3.4]octane or a 6-aza-spiro[3.4]octane ring system; and (c) a cyclopentanopyrrolidine ring system.

1.51 A compound according to Embodiment 1.50 wherein the bicyclic ring system formed by the moiety:

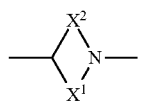

is selected from ring systems BA, BB, BC, CA, CB and DA below:

BA

BB

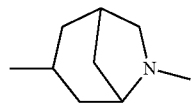
BC

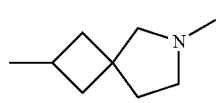
CA

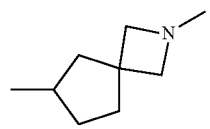
CB

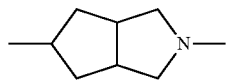
DA 1.52 A compound according to Embodiment 1.1 having the formula (2):

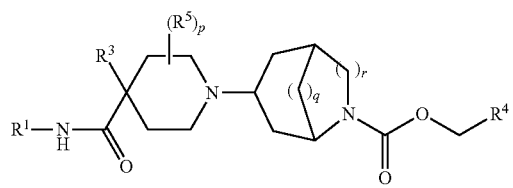
(2)

wherein $R^1$, $R^3$, $R^4$, $R^5$ and p are as defined in any one of Embodiments 1.1 to 1.34; q is 1, 2 or 3 and r is 0 or 1, provided that the total of q and r is 2 or 3.

1.53 A compound according to Embodiment 1.52 wherein (i) r is 0 and q is 2; (ii) r is 0 and q is 3; or (iii) r is 1 and q is 1.

1.54 A compound according to Embodiment 1.1 having the formula (3):

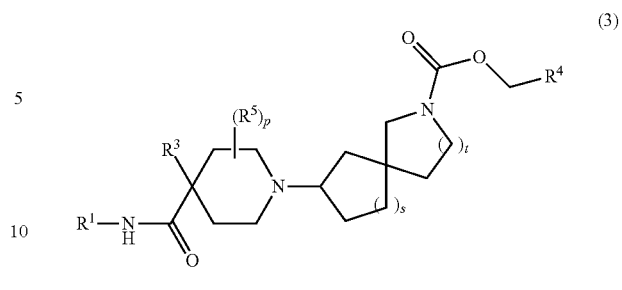
(3)

wherein $R^1$, $R^3$, $R^4$, $R^5$ and p are as defined in any one of Embodiments 1.1 to 1.34; s is 0 or 1 and t is 0 or 1.

1.55. A compound according to Embodiment 1.54 wherein the total of s and t is 1.

1.56 A compound according to Embodiment 1.55 wherein s is 0 and t is 1.

1.57 A compound according to Embodiment 1.55 wherein s is 1 and t is 0.

1.58 A compound according to Embodiment 1.1 having the formula (4):

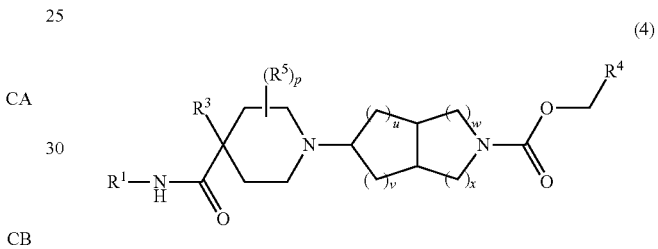
(4)

wherein $R^1$, $R^3$, $R^4$, $R^5$ and p are as defined in any one of Embodiments 1.1 to 1.34; and u, v, w and x are each 0, 1 or 2 provided that the total u+v+w+x is at least 1 and does not exceed 5.

1.59 A compound according to Embodiment 1.58 wherein each of u, v, w and x is 1.

1.60 A compound according to Embodiment 1.1 which is as defined in any one of Examples 1 to 13.

1.61 A compound according to any one of Embodiments 1.1 to 1.60 having a molecular weight of less than 550, for example less than 500, or less than 450.

1.62 A compound according to any one of Embodiments 1.1 to 1.61 which is in the form of a salt.

1.63 A compound according to Embodiment 1.62 wherein the salt is an acid addition salt.

1.64 A compound according to Embodiment 1.62 or Embodiment 1.63 wherein the salt is a pharmaceutically acceptable salt.

Definitions

In this application, the following definitions apply, unless indicated otherwise.

The term "treatment", in relation to the uses of the compounds of the formula (1), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

In formula (1), $X^1$ and $X^2$ are saturated hydrocarbon groups which together contain a total of five to nine carbon atoms and which link together such that the moiety:

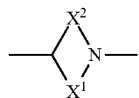

forms a bicyclic ring system. The term "bicyclic ring system" as used herein in the context of $X^1$ and $X^2$ includes fused bicyclic systems, bridged bicyclic systems and spirocyclic systems containing two linked rings.

The term "non-aromatic hydrocarbon group" (as in "$C_{1-10}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" and "cycloalkenyl" are used in their conventional sense (e.g. as defined in the IUPAC Gold Book) unless indicated otherwise.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^3$ and $R^4$ above, where stated, one or two but not all, carbon atoms of the non-aromatic hydrocarbon group may optionally be replaced by a heteroatom selected from O, N and S and (in the case of $R^1$ and $R^4$) oxidised forms thereof. In the definition of the moiety $R^b$ forming part of $R^6$, one or two, but not all, carbon atoms of the hydrocarbon group may optionally be replaced by a heteroatom selected from O, N and S or by a group selected from CO, $X^1C(X^2)$, $C(X^2)X^1$, SO and $SO_2$. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—$S(O)_2$—$CH_2$—, replacement of a carbon atom in a —$CH_2$—$CH_2$—$CH_2$— chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1) can exist in the form of salts, for example acid addition salts or, in certain cases salts of organic and inorganic bases such as carboxylate, sulfonate and phosphate salts. All such salts are within the scope of this invention, and references to compounds of the formula (1) include the salt forms of the compounds as defined in Embodiments 1.62 to 1.64.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.63) may be formed with a wide variety of acids, both inorganic and organic. Examples of acid addition salts falling within Embodiment 1.63 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1 S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic. L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) contain an amine function, these may form quaternary ammonium salts, for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.65), the invention provides a geometric isomer of a compound according to any one of Embodiments 1.1 to 1.64.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.66) the invention provides a compound according to any one of Embodiments 1.1 to 1.65 which contains a chiral center.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415 Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity.

Thus, in certain circumstances, it may be desirable to use as a therapeutic agent only one of a pair of enantiomers, or only one of a plurality of diastereoisomers.

Accordingly, in another embodiment (Embodiment 1.67), the invention provides compositions containing a compound according to Embodiment 1.66 having one or more chiral centres, wherein at least 55% (e.g. at least 60%, 65%, 70%, 75%, 80%, 85%, 90% or 95%) of the compound of Embodiment 1.65 is present as a single optical isomer (e.g. enantiomer or diastereoisomer).

In one general embodiment (Embodiment 1.68), 99% or more (e.g. substantially all) of the total amount of the compound (or compound for use) of Embodiment 1.66 is present as a single optical isomer.

For example, in one embodiment (Embodiment 1.69 the compound is present as a single enantiomer.

In another embodiment (Embodiment 1.70), the compound is present as a single diastereoisomer.

The invention also provides mixtures of optical isomers, which may be racemic or non-racemic. Thus, the invention provides:

1.71 A compound according to Embodiment 1.66 which is in the form of a racemic mixture of optical isomers.

1.72 A compound according to Embodiment 1.66 which is in the form of a non-racemic mixture of optical isomers.

Isotopes

The compounds of the invention as defined in any one of Embodiments 1.1 to 1.72 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.73), the compound of any one of Embodiments 1.1 to 1.72 contains no radioactive isotopes. Such compounds are preferred for therapeutic use.

In another embodiment (Embodiment 1.74), however, the compound of any one of Embodiments 1.1 to 1.72 may contain one or more radioisotopes. Compounds containing such radioisotopes may be useful in a diagnostic context.

Solvates

Compounds of the formula (1) as defined in any one of Embodiments 1.1 to 1.74 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.75 and 1.76, the invention provides:

1.75 A compound according to any one of Embodiments 1.1 to 1.74 in the form of a solvate.

1.76 A compound according to Embodiment 1.75 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.77), the invention provides a compound as defined in any one of Embodiments 1.1 to 1.74 in an anhydrous form (e.g. anhydrous crystalline form).

Crystalline and Amorphous Forms

The compounds of any one of Embodiments 1.1 to 1.77 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari. G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.78 A compound according to any one of Embodiments 1.1 to 1.77 in a crystalline form.

1.79 A compound according to any one of Embodiments 1.1 to 1.77 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.80 A compound according to any one of Embodiments 1.1 to 1.77 which is in an amorphous form.

Prodrugs

The compounds of the formula (1) as defined in any one of Embodiments 1.1 to 1.74 may be presented in the form of a pro-drug. By "prodrugs" is meant for example any compound that is converted in vivo into a biologically active compound of the formula (1), as defined in any one of Embodiments 1.1 to 1.74.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.81), the invention provides a pro-drug of a compound as defined in any one of Embodiments 1.1 to 1.74 wherein the compound contains a functional group which is convertable under physiological conditions to form a hydroxyl group or amino group.

Complexes and Clathrates

Also encompassed by formula (1) in Embodiments 1.1 to 1.81 are complexes (e.g. inclusion complexes or clathrates with compounds such as cyclodextrins, or complexes with metals) of the compounds of Embodiments 1.1 to 1.81.

Accordingly, in another embodiment (Embodiment 1.82), the invention provides a compound according to any one of Embodiments 1.1 to 1.81 in the form of a complex or clathrate.

Biological Activity and Therapeutic Uses

The compounds of the present invention have activity as muscarinic M1 receptor agonists. The muscarinic activity of the compounds can be determined using the Phospho-ERK1/2 assay described in Example A below.

A significant advantage of compounds of the invention is that they are highly selective for the M1 receptor relative to the M2 and M3 receptor subtypes. Compounds of the invention are neither agonists nor antagonists of the M2 and M3 receptor subtypes. For example, whereas compounds of the invention typically have $pEC_{50}$ values of at least 6 (preferably at least 6.5) and $E_{max}$ values of greater than 80 (preferably greater than 95) against the M1 receptor in the functional assay described in Example A, they may have $pEC_{50}$ values of less than 5 and $E_{max}$ values of less than 20% when tested against the M2 and M3 subtypes in the functional assay of Example A.

Accordingly, in Embodiments 2.1 to 2.9, the invention provides:

2.1 A compound according to any one of Embodiments 1.1 to 1.82 for use in medicine.

2.2 A compound according to any one of Embodiments 1.1 to 1.82 for use as a muscarinic M1 receptor agonist.

2.3 A compound according to any one of Embodiments 1.1 to 1.82 which is a muscarinic M1 receptor agonist having a $pEC_{50}$ in the range from 6.0 to 7.9 and an $E_{max}$ of at least 90 against the M1 receptor in the assay of Example A herein or an assay substantially similar thereto.

2.4 A compound according to Embodiment 2.3 which is a muscarinic M1 receptor agonist having a $pEC_{50}$ in the range from 6.5 to 7.5.

2.5 A compound according to Embodiment 2.3 or Embodiment 2.4 having an $E_{max}$ of at least 95 against the M1 receptor.

2.6 A compound according to any one of Embodiments 2.3 to 2.5 which is selective for the M1 receptor compared to the muscarinic M2 and M3 receptors.

2.7 A compound according to any one of Embodiments 2.3 to 2.6 which has a $pEC_{50}$ of less than 5 and an $E_{max}$ of less than 50 against the muscarinic M2 and M3 receptor subtypes.

2.8 A compound according to Embodiment 2.7 which has a $pEC_{50}$ of less than 4.5 and/or an $E_{max}$ of less than 30 against the muscarinic M2 and M3 receptor subtypes.

2.9 A compound according to any one of Embodiments 1.1 to 1.82 and Embodiments 2.3 to 2.8 for use in the treatment of a disease or condition mediated by the muscarinic M1 receptor.

By virtue of their muscarinic M1 receptor agonist activity, compounds of the invention can be used in the treatment of Alzheimer's disease, schizophrenia and other psychotic disorders, cognitive disorders and other diseases mediated by the muscarinic M1 receptor, and can also be used in the treatment of various types of pain.

Accordingly, in Embodiments 2.10 to 2.26, the invention provides:

2.10 A compound according to any one of Embodiments 1.1 to 1.82 for use in the treatment of a cognitive disorder or psychotic disorder.

2.11 A compound for use in according to Embodiment 2.10 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and and schizo-affective disorder.

2.12 A compound according to any one of Embodiments 1.1 to 1.82 for use in the treatment of Alzheimer's disease.

2.13 A compound according to any one of Embodiments 1.1 to 1.82 for use in the treatment of Schizophrenia.

2.14 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.82.

2.15 A method according to Embodiment 2.14 wherein the cognitive disorder comprises, arises from or is associated with a condition as defined in Embodiment 2.11.

2.16 A method according to Embodiment 2.15 wherein the cognitive disorder arises from or is associated with Alzheimer's disease.

2.17 A method according to Embodiment 2.16 wherein the cognitive disorder is Schizophrenia.

2.18 The use of a compound according to any one of Embodiments 1.1 to 1.82 for the manufacture of a medicament for the treatment of a cognitive disorder.

2.19 The use according to Embodiment 2.10 wherein the cognitive disorder comprises, arises from or is associated with a condition as defined in Embodiment 2.11.

2.20 The use according to Embodiment 2.19 wherein the cognitive disorder arises from or is associated with Alzheimer's disease.

2.21 The use according to Embodiment 2.19 wherein the cognitive disorder is Schizophrenia.

2.22 A compound according to any one of Embodiments 1.1 to 1.82 for the treatment or lessening the severity of acute, chronic, neuropathic, or inflammatory pain, arthritis, migraine, duster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.23 A method of treatment or lessening the seventy of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.82.

2.24 A compound according to any one of Embodiments 1.1 to 1.82 for the treatment of peripheral disorders such as reduction of intra ocular pressure in Glaucoma and treatment of dry eyes and dry mouth including Sjogren's Syndrome.

2.25 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.82.

2.26 The use of a compound according to any one of Embodiments 1.1 to 1.82 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.27 The use of a compound according to any one of Embodiments 1.1 to 1.82 for the use in the treatment of skin lesions for example due to pemphigus vulgaris, dermatitis herpetiformis, pemphigoid and other blistering skin conditions.

2.28 The use of a compound according to any one of Embodiments 1.1 to 1.82 for the use in treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhea.

2.29 The use of a compound according to any one of Embodiments 1.1 to 1.82 for the use in in the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.82, which process comprises:

(A) the reaction of a compound of the formula (10)

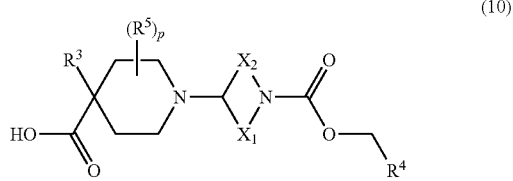

wherein $R^3$, $R^4$, $R^5$, $X_1$ and $X_2$ are as defined in any one of Embodiments 1.1 to 1.82 with a compound of the formula $R^1R^2NH$ under amide-forming conditions; or (B) the reaction of a compound of the formula (11):

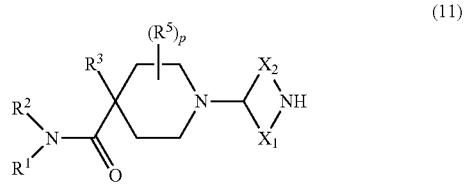

with (i) a compound of the formula $Cl-C(=O)-CH^2-R^4$, in the presence of a base; or (ii) a compound of the formula $R^4-CH_2-OH$ and triphosgene; or (iii) with 4-nitrophenyl chloroformate followed by a compound of the formula $R^4-CH_2-OH$, in the presence of a base;

and optionally:

(C) converting one compound of the formula (1) to another compound of the formula (1).

In process variant (A), the reaction may be carried out in the presence of a reagent of the type commonly used in the formation of amide bonds. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino) phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber,* 103, 708, 2024-2034). A preferred amide coupling agent is HATU.

The coupling reaction is typically carried out in a non-aqueous, non-protic solvent such as acetonitrile, dioxane, dimethylsulphoxide, dichloromethane, dimethylformamide or N-methylpyrrolidinone, or in an aqueous solvent optionally together with one or more miscible co-solvents. The reaction can be carried out at room temperature or, where the reactants are less reactive at an appropriately elevated temperature, for example a temperature up to about 100° C., e.g. 50-80° C. The reaction may optionally be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. The acid chloride is typically reacted with the compound of formula $R^1R^2NH$ in the presence of a base such as sodium bicarbonate. The acid chloride can be prepared using standard methods, for example by treatment of the acid with oxalyl chloride in the presence of a catalytic amount of dimethylformamide.

Process variant (B) is typically carried out in an aprotic solvent such as dichloromethane or dichloroethane in the presence of a non-interfering base such as triethylamine. The reaction may be conducted at room temperature.

Intermediate compounds of the formula (10) can be prepared by the series of reactions shown in Scheme 1 below.

Scheme 1

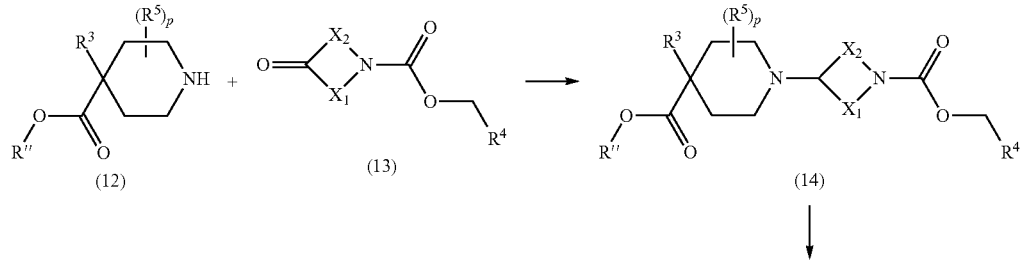

-continued

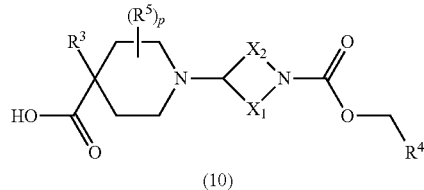

(10)

In reaction Scheme 1, the piperidine ester (12, R"=ethyl or methyl) is reacted with the substituted ketone (13) under reductive amination conditions. The reductive amination reaction is typically carried out with mild heating (e.g. to a temperature of from about 40° C. to about 70° C.) in the presence of either sodium cyanoborohydride in combination with zinc chloride or sodium triacetoxyborohydride in combination with titanium isopropoxide in a solvent such as dichloromethane or dichloroethane containing acetic acid to give an intermediate ester compound (14) which is then selectively hydrolysed under mild conditions using lithium hydroxide or sodium hydroxide to give compound (10).

Compounds of the formula (11) can be prepared by the sequence of reactions shown in Scheme 2 below.

Scheme 2

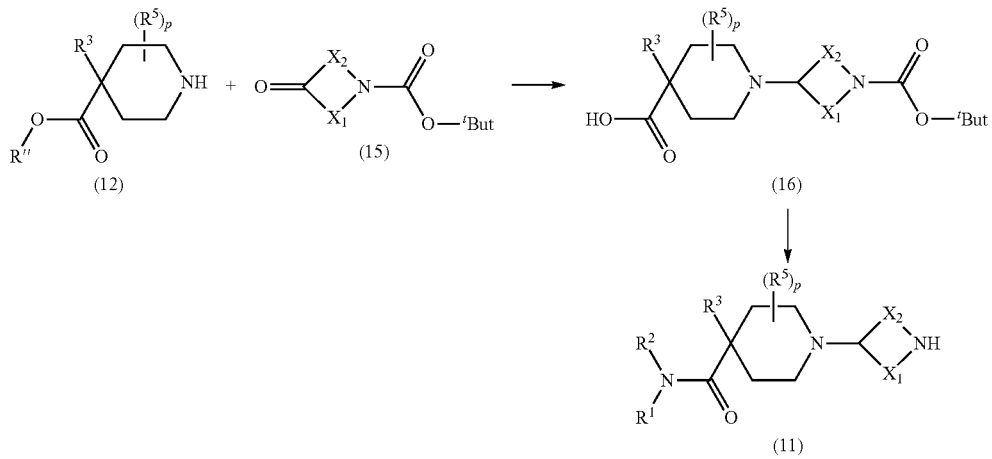

In Scheme 2, the piperidine ester (12, R"=ethyl or methyl) is reacted with the ketone (15) under reductive amination conditions of the type described above to give an intermediate ester (not shown) which is then selectively hydrolysed using lithium hydroxide to give the carboxylic acid (16). The carboxylic acid (16) is then reacted with an amine $HNR^1R^2$ under amide-forming conditions (see above) to give an intermediate amide compound (not shown) which is then deprotected by removal of the Boc group by treatment with acid (e.g. trifluoroacetic acid in dichloromethane) to give the compound (11).

Compounds of the formula (10) can also be prepared by the sequence of reactions shown in Scheme 3 below.

Scheme 3

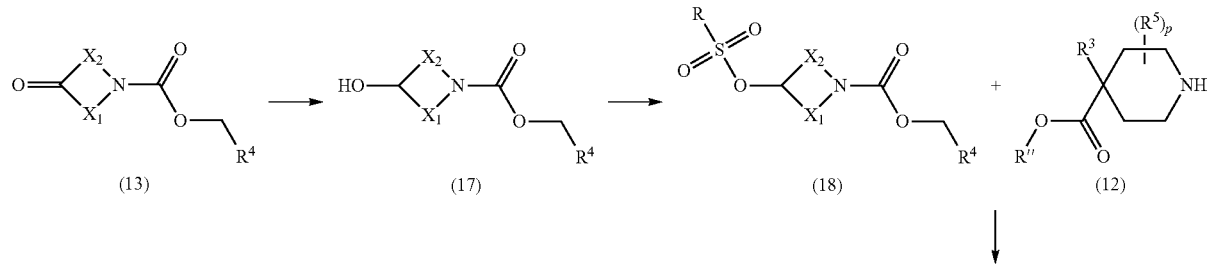

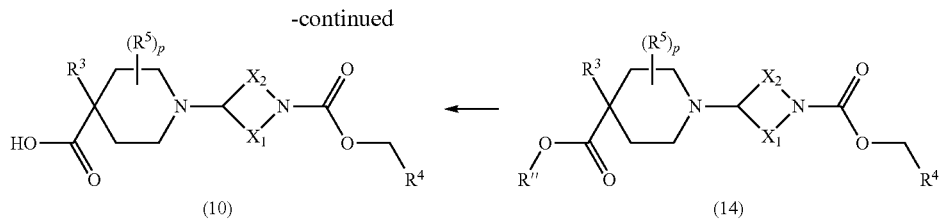

In Scheme 3, the substituted ketone (13) is reduced to the alcohol (17) using sodium borohydride in methanol. The alcohol (17) is then activated as the sulfonic ester (18, R=methyl, trifluormethyl or 4-methylphenyl) using the corresponding sulfonyl chloride in dichloromethane in the presence of a tertiary amine such as triethylamine or N,N-diisopropylethylamine. The sulfonic ester (18) is reacted with the piperidine ester (12, R"=ethyl or methyl) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide to give compound (14) which is then selectively hydrolysed under mild conditions using lithium hydroxide or sodium hydroxide to give compound (10).

Once formed, one compound of the formula (1), or a protected derivative thereof, can be converted into another compound of the formula (1) by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.82 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1 to 32

The compounds of Examples 1 to 32 shown in Table 1 below have been prepared. Their NMR and LCMS properties and the methods used to prepare them are set out in Table 3. The starting materials for each of the Examples are listed in Table 2.

TABLE 1

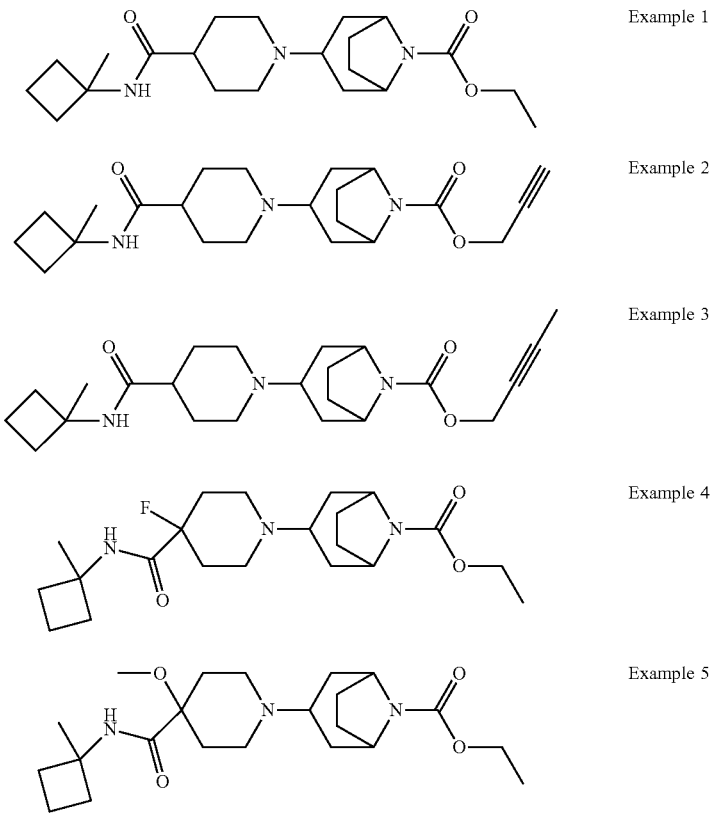

TABLE 1-continued
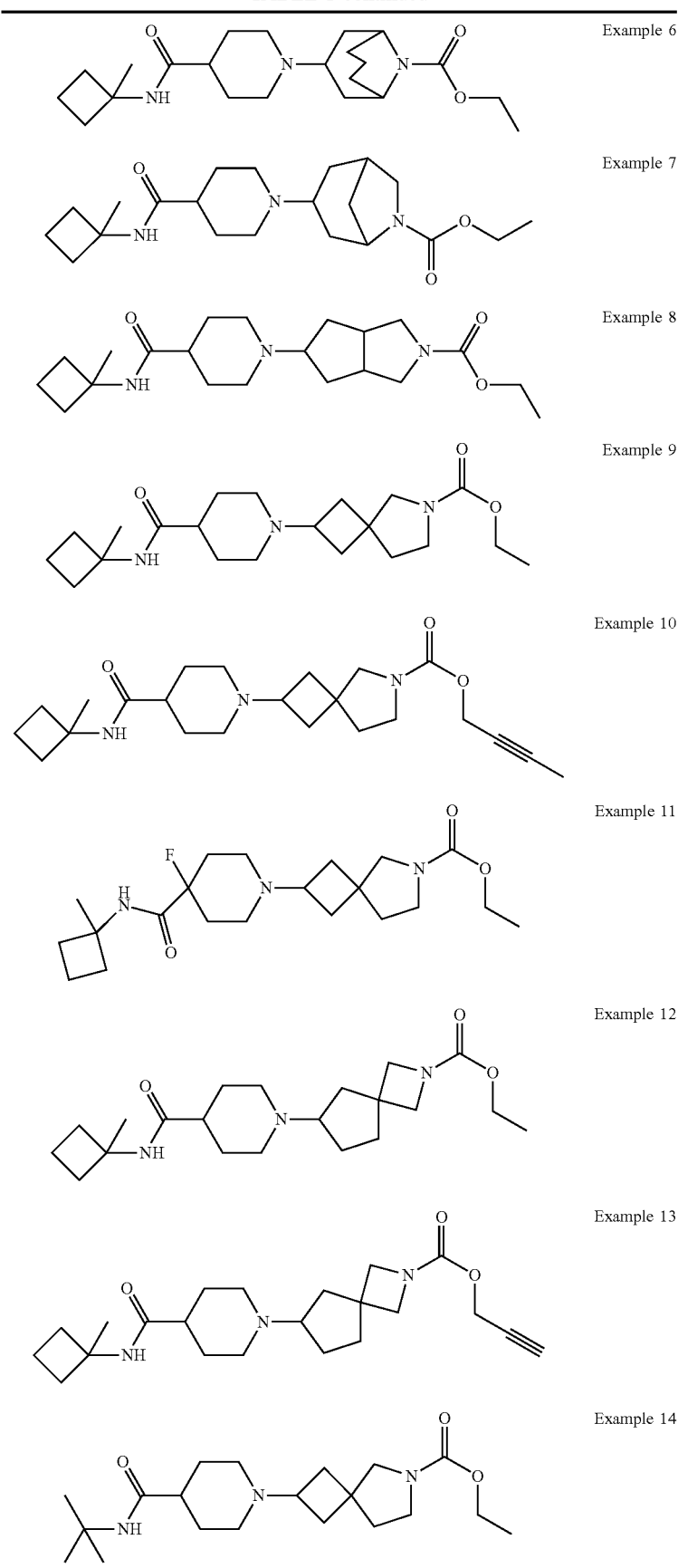
Example 6
Example 7
Example 8
Example 9
Example 10
Example 11
Example 12
Example 13
Example 14

TABLE 1-continued
| | |
|---|---|
| 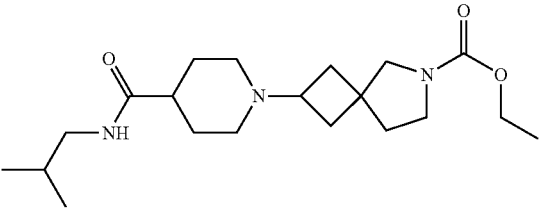 [SMILES: CCOC(=O)N1CCC2(CC(N3CCC(C(=O)NCC(C)C)CC3)C2)C1] | Example 15 |
| 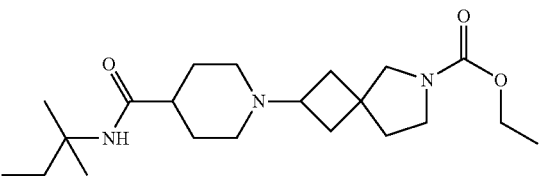 [SMILES: CCOC(=O)N1CCC2(CC(N3CCC(C(=O)NC(C)(C)CC)CC3)C2)C1] | Example 16 |
| 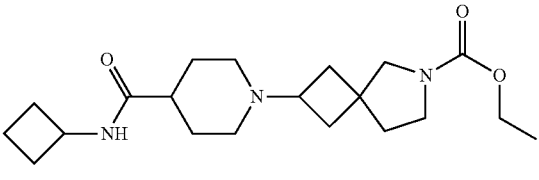 [SMILES: CCOC(=O)N1CCC2(CC(N3CCC(C(=O)NC4CCC4)CC3)C2)C1] | Example 17 |
| 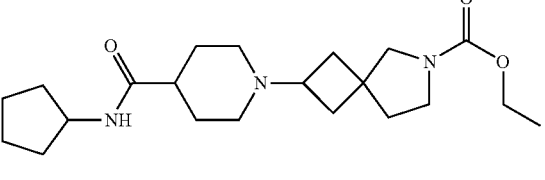 | Example 18 |
| 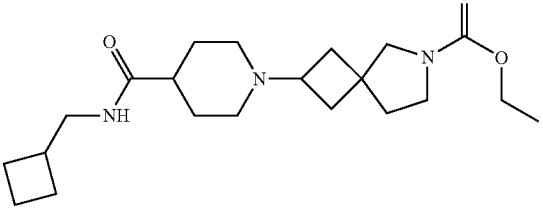 | Example 19 |
| 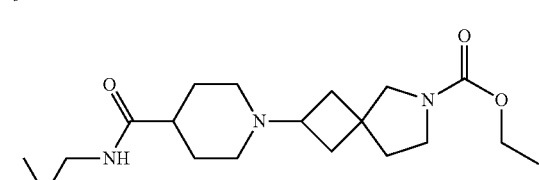 | Example 20 |
| 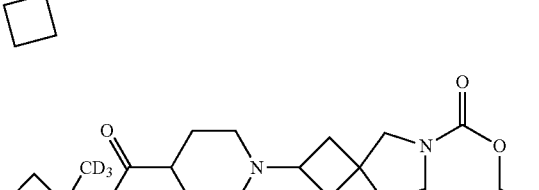 | Example 21 |
| 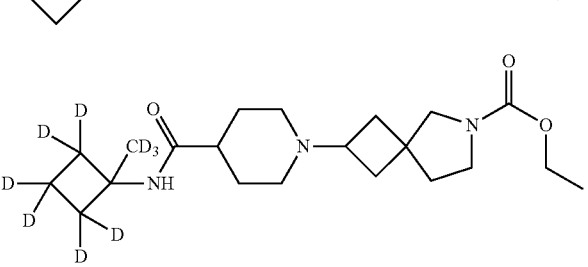 | Example 22 |

TABLE 1-continued
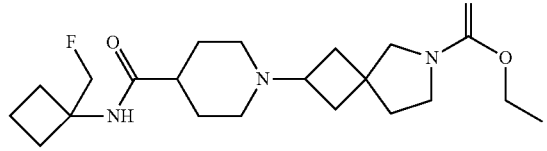
Example 23
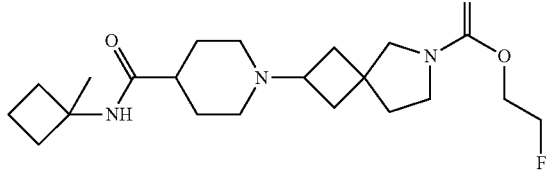
Example 24
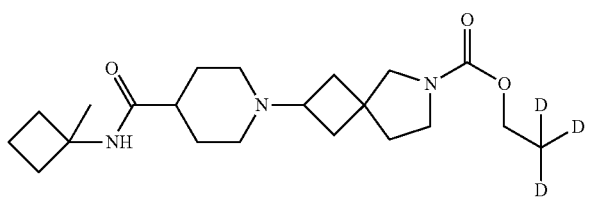 [SMILES: [2H]C([2H])([2H])COC(=O)N1CCC2(CC(N3CCC(C(=O)NC4(C)CCC4)CC3)C2)C1]
Example 25
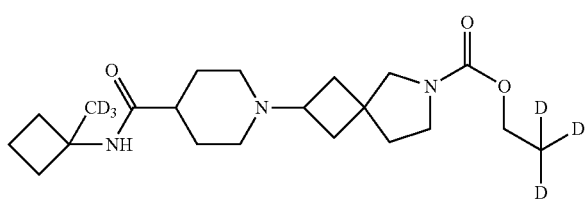 [SMILES: [2H]C([2H])([2H])COC(=O)N1CCC2(CC(N3CCC(C(=O)NC4(C([2H])([2H])[2H])CCC4)CC3)C2)C1]
Example 26
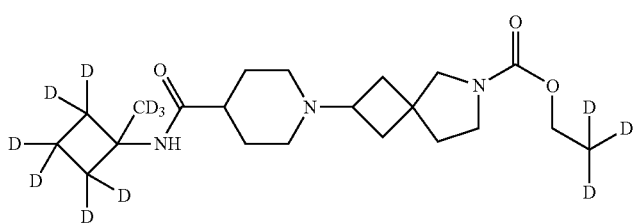 [SMILES: [2H]C([2H])([2H])COC(=O)N1CCC2(CC(N3CCC(C(=O)NC4(C([2H])([2H])[2H])C([2H])([2H])C([2H])([2H])C4([2H])[2H])CC3)C2)C1]
Example 27
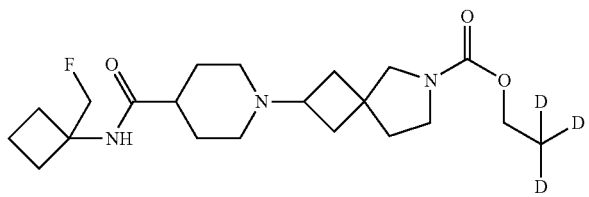 [SMILES: [2H]C([2H])([2H])COC(=O)N1CCC2(CC(N3CCC(C(=O)NC4(CF)CCC4)CC3)C2)C1]
Example 28
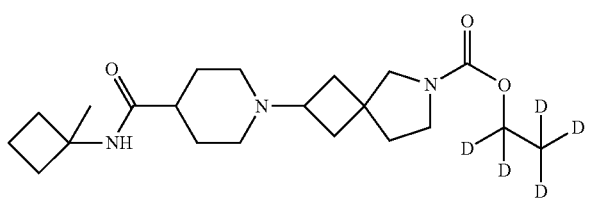 [SMILES: [2H]C([2H])([2H])C([2H])([2H])OC(=O)N1CCC2(CC(N3CCC(C(=O)NC4(C)CCC4)CC3)C2)C1]
Example 29
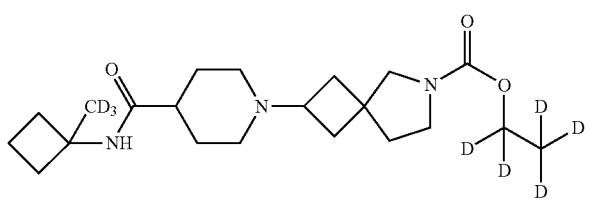 [SMILES: [2H]C([2H])([2H])C1(NC(=O)C2CCN(C3CC4(CCN(C(=O)OC([2H])([2H])C([2H])([2H])[2H])C4)C3)CC2)CCC1]
Example 30

TABLE 1-continued

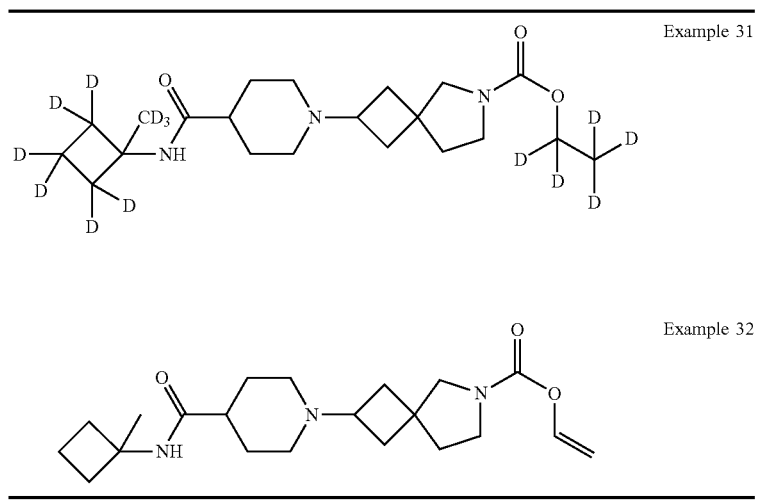

Example 31

Example 32

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and the Silica gel F254 as a stationary phase from Merck. Microwave-mediated reactions were performed in Biotage Initiator or CEM Discover microwave reactors.

Mass spectroscopy was carried out on Shimadzu LC-2010 EV, Waters ZQ-2000, UPLC-Mass SQD-3100 or Applied Biosystem API-2000 spectrometers using electrospray conditions as specified for each compound in the detailed experimental section.

Preparative HPLC was typically carried out under the following conditions, (Gilson Semi-Prep HPLC): Column: Phenomenex Gemini NX 5 μm C18 110A Axia (100×30 mm); Mobile phase: Solvent A: MeCN; Solvent B: Water containing a 0.1 or 0.2% solution of aqueous $NH_3$ (28%) and 5% MeCN; Gradient: 20 to 60% of Solvent A in Solvent B over 14.4 min, hold 60% Solvent A in Solvent B for 1.6 min, 100% Solvent A for 1.6 min Flowrate: 30 mL/min; Detection wavelength: 210 nm.

LCMS experiments were typically carried out using electrospray conditions as specified for each compound under the following conditions:

Method A and B

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method A: 0.00/2, 0.10/2, 2.50/95, 3.50/95, 3.55/2, 4.00/2 or Method B: 0.00/2, 0.10/2, 8.40/95, 9.40/95, 9.50/2, 10.00/2; Solvents: solvent C=2.5 L $H_2O$+2.5 mL ammonia solution; solvent D=2.5 L MeCN+135 mL $H_2O$+2.5 mL ammonia solution); Injection volume 3 uL; UV detection 230 to 400 nM; column temperature 45° C.; Flow rate 1.5 mL/min.

Method C

Instruments: HP1100, HP DAD G1315A detector, Micromass ZQ; Column: Phenomenex Gemini-NX C-18, 3 micron, 2.0×30 mm; Gradient [time (min)/solvent D in C (%)]: Method C: 0.00/2, 0.10/2, 8.40/95, 9.40/95, 9.50/2, 10.00/2; Solvents: solvent C=2.5 L $H_2O$+2.5 mL ammonia solution; solvent D=2.5 L MeCN+135 mL $H_2O$+2.5 mL ammonia solution); Injection volume 3 uL; UV detection 230 to 400 nM; column temperature 45° C.; Flow rate 1.5 mL/min.

Method D

Instruments: Waters Alliance 2795, Waters 2996 PDA detector, Micromass ZQ; Column: Waters X-Bridge C-18, 2.5 micron, 2.1×20 μm, flow rate 1.0 mL/min; inj volume 5 μL; 5-95% acetonitrile:water+0.1% ammonium hydroxide.

Method E

Instruments: Waters 2695 Alliance, Micromass ZQ, 2996 PDA and a Varian 385-LC ELSD, Column: XBridge C18 3×100 mm×3.5 μm, flow rate 1 mL/min; Inj volume 20 μL, 5-95% acetonirtile:water+2% formic acid GC experiments were run under the following conditions:

Method F

Instruments: Agilent 6890, CP select 624 column; Inj 200° C., 10 psi $H_2$; Det 250° C., 25 mL/min $H_2$, 400 mL/min air; oven 35° C. (2 min) 8° C./min to 130° C. (4.1 min)

Method G

Instruments: Agilent 6890, CP select 624 column; Inj 200° C., 10 psi $H_2$; Det 250° C., 25 mL/min $H_2$, 400 ml/min air; oven 35° C. (2 min) 4° C./min to 130° C. (5.75 min) GC data in the experimental section are given in the format: run time, retention time, percentage peak area.
Abbreviations
d=day(s)
DCM=dichloromethane
DIPEA=diisopropylethylamine
DMF=dimethylformamide
DMSO=dimethylsulfoxide
ES=electro spray ionisation
EtOAc=ethyl acetate
h=hour(s)
HPLC=high performance liquid chromatography
LC=liquid chromatography
MeCN=acetonitrile
MeOH=methanol
min=minute(s)
MS=mass spectrometry
NMR=nuclear magnetic resonance
rt=room temperature
sat.=saturated
sol.=solution
STAB=sodium triacetoxyborohydride
THF=tetrahydrofuran
TLC=thin layer chromatography Prefixes n-, s-, i-, t- and tert- have their usual meanings: normal, secondary, iso, and tertiary.

General Synthetic Procedures

Route a

Typical Procedure for the Preparation of Amides Via STAB Reductive Amination and HATU Coupling as Exemplified by the Preparation of Example 1 Isomer 1, ethyl 3-{4-[(1-methylcyclobutyl)carbamoyl]piperidin-1-yl}-8-azabicyclo[3.2.1]octane-8-carboxylate chromatography (normal phase, [Biotage SNAP cartridge KP-sil 50 g, 40-63 μm, 60 Å, 50 mL per min, gradient 2% to 4.5% MeOH in DCM]) to give ethyl 3-[4-(ethoxycarbonyl)piperidin-1-yl]-8-azabicyclo[3.2.1]octane-8-carboxylate as a separable mixture of isomers. Isomer 1 (0.549 g, 32%) as a light yellow oil and isomer 2 (0.137 g, 8%) as a light yellow oil.

LCMS (Method A): Isomer 1 m/z 339 (M+H)$^+$ (ES$^+$), at 1.78 min, UV inactive.

LCMS (Method A): Isomer 2 m/z 339 (M+H)$^+$ (ES$^+$), at 1.68 min, UV inactive.

Isomer 1 of ethyl 3-[4-(ethoxycarbonyl)piperidin-1-yl]-8-azabicyclo[3.2.1]octane-8-carboxylate (0.549 g, 1.62 mmol) was dissolved in THF (10 mL) at rt and 1 M LiOH sol. (1.62 mL) was added. The reaction mixture was stirred at rt for 2 days. The pH was carefully adjusted to pH 6 by addition of concentrated hydrochloric acid, the solvents were removed in vacuo, to give 1-[8-(ethoxycarbonyl)-8-azabicyclo[3.2.1]oct-3-yl]piperidine-4-carboxylic acid (0.50 g, 100%) as an off white solid.

LCMS (Method A): m/z 311 (M+H)$^+$ (ES$^+$), at 0.1 min, UV inactive

1-[8-(Ethoxycarbonyl)-8-azabicyclo[3.2.1]oct-3-yl]piperidine-4-carboxylic acid (0.50 g assumed 1.62 mmol) was dissolved in DMF (8 mL) and (1-methylcyclobutyl)amine hydrochloride (0.295 g, 2.44 mmol), HATU (0.926 g, 2.44 mmol) and DIPEA (1.05 g, 1.41 mL, 8.12 mmol) were added. The reaction mixture was stirred at rt for 60 h and the solvents were removed in vacuo. The residue was partitioned between DCM and sat. NaHCO$_3$ sol., the organic layer was washed with sat. NaCl sol. and passed through a phase separator cartridge. The solvents of the organic filtrate were removed in vacuo, and the residue was purified by column chromatography (normal phase, [Biotage SNAP cartridge KP-sil 25 g, 40-6 3 μm, 60 Å, 25 mL per min,

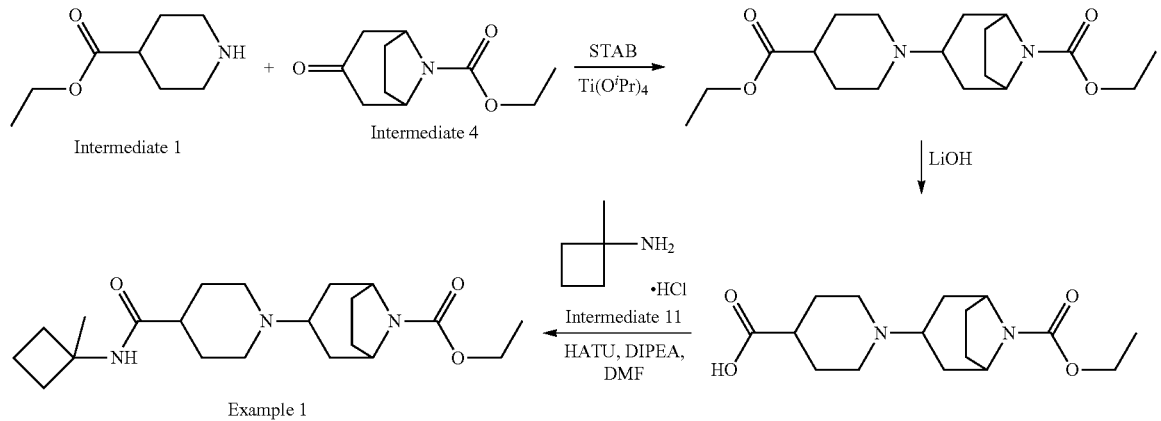

Example 1

Ethyl piperidine-4-carboxylate (0.797 g, 0.78 mL 5.07 mmol) and N-ethoxycarbonylnortropinone (1.00 g, 5.07 mmol) were dissolved in DCM (30 mL) at rt and titanium isopropoxide (1.59 g, 1.7 mL, 5.58 mmol) was added. The reaction mixture was stirred at rt for 1.5 h. STAB (2.15 g, 10.14 mmol) and acetic acid (0.2 mL) were added and the reaction mixture was stirred at rt overnight under nitrogen. The reaction mixture was quenched with the addition of water (4 mL) and diluted with DCM then filtered through a pad of celite. The filtrate was washed with sat. NaHCO$_3$ sol., sat. NaCl sol. and dried over MgSO$_4$. The solvents were removed in vacuo, and the residue was purified by column gradient 0% to 10% MeOH in DCM]) to give ethyl 3-{4-[(1-methylcyclobutyl)carbamoyl]piperidin-1-yl}-8-azabicyclo[3.2.1]octane-8-carboxylate isomer 1 (0.208 g, 34%) as a light yellow gum.

Data in Table 3

Route b

Typical Procedure for the Preparation of Amides Via NaCNBH$_3$ Reductive Amination and HATU Coupling, as Exemplified by the Preparation of Example 5 Isomer 1, ethyl 3-{4-methoxy-4-[(1-methylcyclobutyl)carbamoyl]piperidin-1-yl}-8-azabicyclo[3.2.1]octane-8-carboxylate

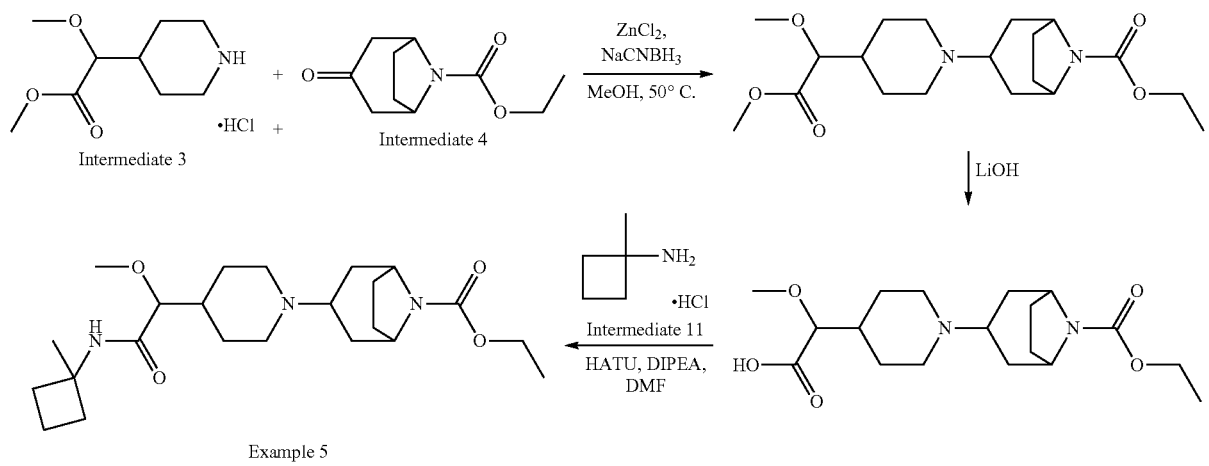

Example 5

4-Methoxypiperidine-4-carboxylic acid methyl ester hydrochloride (0.500 g, 2.38 mmol) was dissolved in methanol (2 mL) and treated with K$_2$CO$_3$ (0.329 g, 2.38 mmol) in a minimum of water to de-salt. The mixture was concentrated in vacuo and azeotroped to dryness with toluene. The residue and N-ethoxycarbonylnortropinone (0.470 g, 2.39 mmol) were dissolved in methanol (20 mL) and zinc chloride (0.975 g, 7.15 mmol) was added. The reaction mixture was stirred at 50° C., under a nitrogen atmosphere, for 2 h then cooled to rt. NaCNBH$_3$ (0.299 g, 4.77 mmol) was added and the reaction mixture was stirred at 50° C. overnight under nitrogen. The reaction mixture was cooled to rt and the solvents were removed in vacuo, the residue was diluted with DCM and treated with sat NaHCO$_3$ sol., the resulting heterogeneous mixture was filtered through a celite pad and the filtrate was washed with sat. NaHCO$_3$ sol., sat NaCl sol. and dried over MgSO$_4$. The solvents were removed in vacuo, and the residue was purified by column chromatography (normal phase, [Biotage SNAP cartridge KP-sil 25 g, 40-63 μm, 60 Å, 50 mL per min, gradient 0% to 10% MeOH in DCM]) to give ethyl 3-[4-methoxy-4-(methoxycarbonyl) piperidin-1-yl]-8-azabicyclo[3.2.1]octane-8-carboxylate as a separable mixture of isomers. Isomer 1 (0.097 g, 12%) as a pale yellow oil and Isomer 2 (0.022 g, 2.5%) as a pale yellow oil.

LCMS (Method A): Isomer 1 m/z 355 (M+H)$^+$ (ES$^+$), at 1.47-1.50 min, UV inactive.

LCMS (Method A): Isomer 2 m/z 355 (M+H)$^+$ (ES$^+$), at 1.47 min, UV inactive.

Isomer 1 of ethyl 3-[4-methoxy-4-(methoxycarbonyl)piperidin-1-yl]-8-azabicyclo[3.2.1]octane-8-carboxylate (0.097 g, 0.27 mmol) was dissolved in THF (5 mL) at rt and 1 M LiOH sol. (0.3 mL) was added. The reaction mixture was stirred at rt for 7 days. The pH was carefully adjusted to pH 6 by addition of concentrated hydrochloric acid, the solvents were removed in vacuo, to give 1-[8-(ethoxycarbonyl)-8-azabicyclo[3.2.1]oct-3-yl]-4-methoxypiperidine-4-carboxylic acid (0.093 g, 100%) as an off white solid.

LCMS (Method A): m/z 341 (M+H)$^+$ (ES$^+$), at 0.83 min, UV inactive.

1-[8-(Ethoxycarbonyl)-8-azabicyclo[3.2.1]oct-3-yl]-4-methoxypiperidine-4-carboxylic acid (0.093 g, assumed 0.27 mmol) was dissolved in DMF (5 mL) and (1-methylcyclobutyl)amine hydrochloride (0.05 g, 0.411 mmol), HATU (0.156 g, 0.41 mmol) and DIPEA (0.177 g, 0.24 mL, 1.37 mmol) were added. The reaction mixture was stirred at rt for 60 h and the solvents were removed in vacuo. The residue was partitioned between DCM and sat. NaHCO$_3$ sol., the organic layer was washed with sat. NaCl sol. and dried (MgSO$_4$). The solvents were removed in vacuo, and the residue was purified by column chromatography (normal phase, [Biotage SNAP cartridge KP-sil 10 g, 40-63 μm, 60 Å, 25 mL per min, gradient 0% to 10% MeOH in DCM]) to give ethyl 3-{4-methoxy-4-[(1-methylcyclobutyl)carbamoyl]piperidin-1-yl}-8-azabicyclo[3.2.1]octane-8-carboxylate isomer 1 (0.028 g, 25%) as a pale yellow gum.

Data in Table 3

Route c

Typical Procedure for the Preparation of Carbamates Via Chloroformate Coupling, as Exemplified by the Preparation of Example 9, ethyl 2-{4-[(1-methylcyclobutyl) carbamoyl] piperidin-1-yl}-6-azaspiro[3.4]octane-6-carboxylate

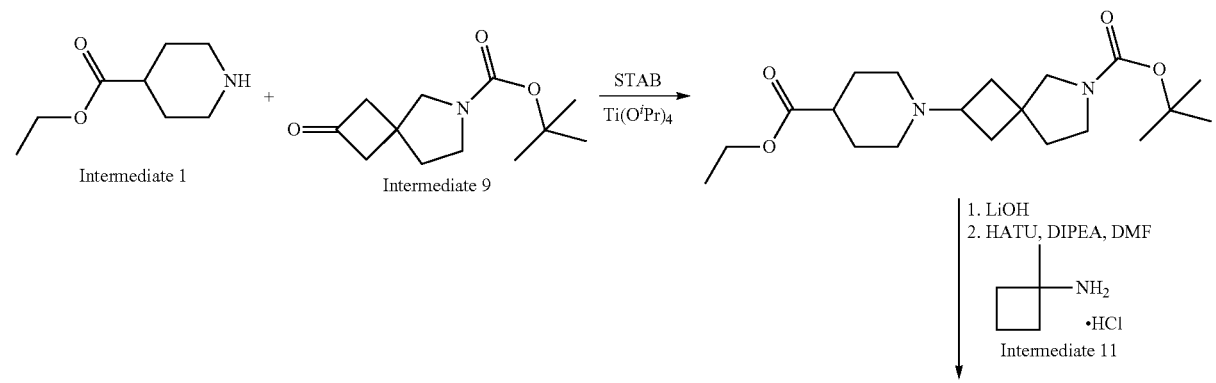

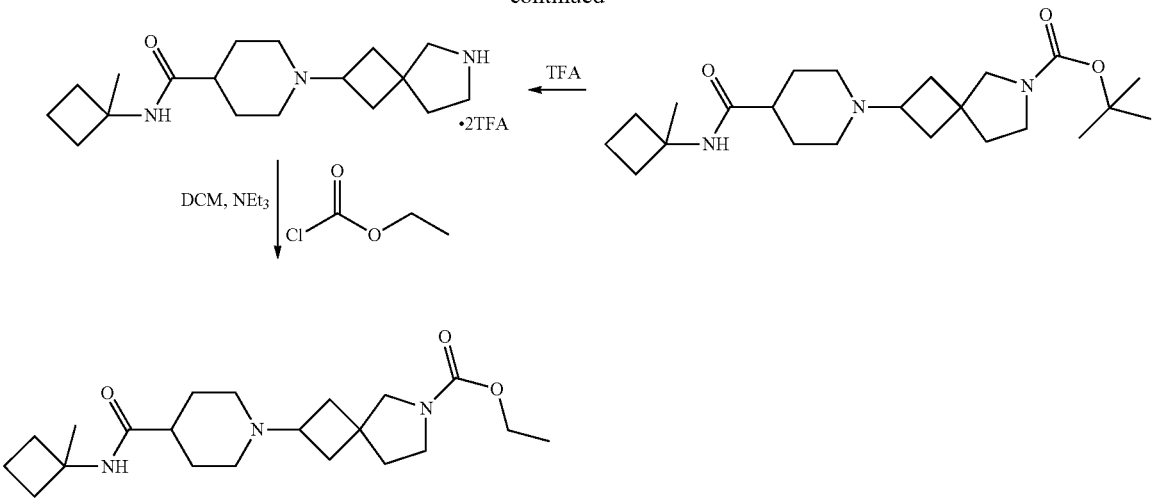

Example 9

Ethyl piperidine-4-carboxylate (0.35 g, 0.32 mL, 2.22 mmol) and 6-azaspiro[3.4]octane-6-carboxylic acid, 2-oxo-,1,1-dimethylethyl ester (0.500 g, 2.22 mmol) were dissolved in DCM (20 mL) at rt and titanium isopropoxide (4.12 g, 4.40 mL, 14.5 mmol) was added. The reaction mixture was stirred at rt for 1 h. STAB (0.694 g, 0.72 mL, 2.44 mmol) and acetic acid (0.05 mL) were added and the reaction mixture was stirred at rt overnight under nitrogen. The reaction mixture was quenched with the addition of sat NaHCO₃ sol (5 mL) and stirred for 5 minutes. The reaction mixture was diluted with DCM and filtered through a pad of celite. The filtrate was separated and washed with sat NaCl sol. and dried over MgSO₄. The solvents were removed in vacuo, and the residue was purified by column chromatography (normal phase, [Biotage SNAP cartridge KP-sil 50 g, 40-63 μm, 60 Å, 50 mL per min, gradient 0% to 5% MeOH in DCM]) to give tert-butyl 2-[4-(ethoxycarbonyl)piperidin-1-yl]-6-azaspiro[3.4]octane-6-carboxylate (0.739 g, 90.9%) as a pale yellow oil.

LCMS (Method A): m/z 367 (M+H)⁺ (ES⁺), at 1.94/1.99 min, UV inactive tert-Butyl 2-[4-(ethoxycarbonyl)piperidin-1-yl]-6-azaspiro[3.4]octane-6-carboxylate (0.739 g, 2.02 mmol) was dissolved in THF (10 mL) at rt and 1 M LiOH sol. (2.02 mL) was added. The reaction mixture was stirred at rt overnight. The reaction mixture was adjusted to pH 5 by addition of 1 M HCl sol. and solvents were removed in vacuo, to give 1-[6-(tert-butoxycarbonyl)-6-azaspiro[3.4]oct-2-yl]piperidine-4-carboxylic acid, which was used crude in the subsequent reaction.

LCMS (Method A): m/z 339 (M+H)⁺ (ES⁺), at 0.12 min, UV inactive

1-[6-(tert-Butoxycarbonyl)-6-azaspiro[3.4]oct-2-yl]piperidine-4-carboxylic acid was dissolved in DMF (5 mL) and (1-methylcyclobutyl)amine hydrochloride (0.37 g, 3.03 mmol), HATU (0.844 g, 2.22 mmol) and DIPEA (1.305 g, 10.1 mmol) were added. The reaction mixture was stirred at rt overnight under nitrogen. The solvents were removed in vacuo, and the residue was partitioned between DCM and sat NaHCO₃ sol., organic layer washed with sat NaCl sol. and dried over MgSO₄. The solvents were removed in vacuo, and the residue was purified by column chromatography (normal phase, [Biotage SNAP cartridge KP-sil 50 g, 40-63 μm, 60 Å, 50 mL per min, gradient 0% to 10% MeOH in DCM]) to give tert-butyl 2-{4-[(1-methylcyclobutyl)carbamoyl]piperidin-1-yl}-6-azaspiro[3.4]octane-6-carboxylate (0.627 g, 76.7%) as a white foam.

LCMS (Method A): m/z 406 (M+H)⁺ (ES⁺), at 1.81 min, UV inactive tert-Butyl 2-{4-[(1-methylcyclobutyl)carbamoyl]piperidin-1-yl}-6-azaspiro[3.4]octane-6-carboxylate (0.627 g, 1.55 mmol) was dissolved in DCM (8 mL) and TFA (2 mL) was added. The reaction mixture was stirred at rt overnight under nitrogen, then the solvents were removed in vacuo, to give 1-(6-azaspiro[3.4]oct-2-yl)-N-(1-methylcyclobutyl)piperidine-4-carboxamide trifluoroacetate as a dark yellow oil which was used directly without further purification. The residue was dissolved in DCM (10 mL) and NEt₃ (0.49 g, 0.65 mL, 4.64 mmol) and ethyl chloroformate (0.25 mg, 0.18 mL, 0.57 mmol) were added and the reaction mixture was stirred at rt overnight under nitrogen. The solvents were removed in vacuo, and the residue was partitioned between DCM and sat NaHCO₃ sol., organic layer washed with sat NaCl sol. and dried over MgSO₄. The residue was purified by column chromatography (normal phase, [Biotage SNAP cartridge KP-sil 10 g, 40-63 μm, 60 Å, 12 mL per min, gradient 0% to 10% MeOH in DCM]) to give ethyl 2-{4-[(1-methylcyclobutyl)carbamoyl]piperidin-1-yl}-6-azaspiro[3.4]octane-6-carboxylate (0.04 g, 13%) as a yellow gum as a mixture of diastereomers.

Data in Table 3

Route d

Typical Procedure for the Preparation of Single Diastereoisomers, Followed by Chloroformate Coupling, as Exemplified by the Preparation of Example 9 Isomer 2, ethyl 2-{4-[(1-methylcyclobutyl)carbamoyl]piperidin-1-yl}-6-azaspiro[3.4]octane-6-carboxylate

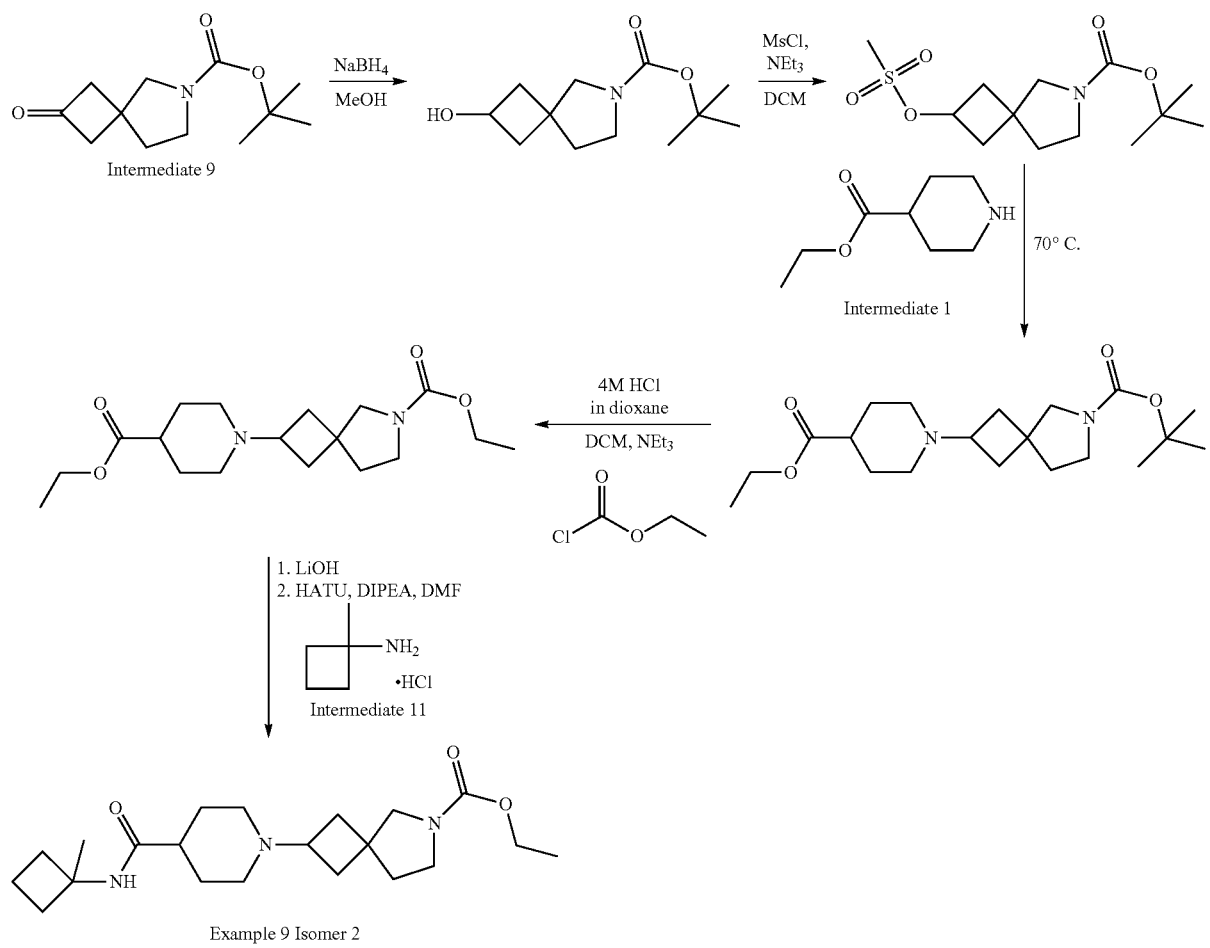

Example 9 Isomer 2

6-Azaspiro[3.4]octane-6-carboxylic acid, 2-oxo-, 1,1-dimethylethyl ester (3.00 g, 13.33 mmol) was reduced to the alcohol, reacted under mesylation conditions and the resulting diastereoisomers were separated in accordance with information detailed in patent WO 2010/089510, to produce tert-butyl 2-[(methylsulfonyl)oxy]-6-azaspiro[3.4]octane-6-carboxylate isomer 1 (1.79 g, 44% over two steps) as a white crystalline solid and isomer 2 (0.965 g, 24% over two steps) as a white crystalline solid.

LCMS (Method B): Isomer 1; m/z 306 (M+H)$^+$ (ES$^+$), at 3.36 min, UV inactive

LCMS (Method B): Isomer 2; m/z 306 (M+H)$^+$ (ES$^+$), at 3.39 min, UV inactive tert-Butyl 2-[(methylsulfonyl)oxy]-6-azaspiro[3.4]octane-6-carboxylate isomer 1 (1.79 g, 5.73 mmol) and ethyl isonipecotate (4.49 g, 28.62 mmol) were heated together to 65° C. for 5 days. The reaction mixture was reduced in volume in vacuo, and the residue was purified by column chromatography (normal phase, [Biotage SNAP cartridge KP-sil 100 g, 40-63 μm, 60 Å, 50 mL per min, gradient 1% to 4.5% MeOH in DCM]) to give tert-butyl 2-[4-(ethoxycarbonyl)piperidin-1-yl]-6-azaspiro[3.4]octane-6-carboxylate (0.264 g, 12.5%) as a yellow oil.

LCMS (Method A): m/z 367 (M+H)$^+$ (ES$^+$), at 1.97 min, UV inactive.

tert-Butyl 2-[4-(ethoxycarbonyl)piperidin-1-yl]-6-azaspiro[3.4]octane-6-carboxylate (0.080 g, 0.22 mmol) was stirred in DCM (10 mL) at rt and treated with 4 M HCl/dioxane (1 mL). The reaction mixture was stirred overnight at room temperature. The reaction mixture was conc. in vacuo to give a yellow solid that was used directly without further purification. The residue was dissolved in DCM (10 mL) and NEt$_3$ (0.066 g, 0.1 mL, 0.66 mmol) and ethyl chloroformate (0.036 g, 0.03 mL, 0.32 mmol) were added and the reaction mixture was stirred at rt overnight under nitrogen. The solvents were removed in vacuo, and the residue was partitioned between DCM and sat. NaHCO$_3$ sol., organic layer washed with sat. NaCl sol. and dried over MgSO$_4$. The residue was purified by column chromatography (normal phase, [Biotage SNAP cartridge KP-sil 10 g, 40-63 μm, 60 Å, 12 mL per min, gradient 0% to 8% MeOH in DCM]) to give ethyl 2-[4-(ethoxycarbonyl)piperidin-1-yl]-6-azaspiro[3.4]octane-6-carboxylate (0.069 g, 93%) as an amber oil.

LCMS (Method A): m/z 339 (M+H)$^+$ (ES$^+$), at 1.71 min, UV inactive.

Ethyl 2-[4-(ethoxycarbonyl)piperidin-1-yl]-6-azaspiro[3.4]octane-6-carboxylate (0.069 g, 0.20 mmol) was dissolved in THF (4 mL) at rt and 1 M LiOH sol. (0.31 mL) was added. The reaction mixture was stirred at rt over the weekend. The reaction mixture was adjusted to pH 5 by addition of 1 M HCl sol. and solvents were removed in vacuo, to give 1-[6-(ethoxycarbonyl)-6-azaspiro[3.4]oct-2-yl]piperidine-4-carboxylic acid which was used directly without further purification.

LCMS (Method A): m/z 311 (M+H)$^+$ (ES$^+$), at 0.10 min, UV inactive.

1-[6-(Ethoxycarbonyl)-6-azaspiro[3.4]oct-2-yl]piperidine-4-carboxylic acid (0.368 g, 1.10 mmol) was dissolved in DMF (8 mL) and (1-methylcyclobutyl)amine hydrochloride (0.200 g, 1.64 mmol), HATU (0.458 g, 1.21 mmol) and DIPEA (0.708 g, 5.45 mmol) were added. The reaction mixture was stirred at rt overnight under nitrogen. The solvents were removed in vacuo, and the residue was partitioned between DCM and sat. NaHCO$_3$ sol., organic layer washed with sat. NaCl sol. and dried over MgSO$_4$. The solvents were removed in vacuo, and the residue was purified by column chromatography (normal phase, [Biotage SNAP cartridge KP-sil 25 g, 40-63 μm, 60 Å, 12 mL per min, gradient 1% to 8% MeOH in DCM]) to give ethyl 2-{4-[(1-methylcyclobutyl)carbamoyl]piperidin-1-yl}-6-azaspiro[3.4]octane-6-carboxylate isomer 2 (0.147 g, 35.5%) as a white foam.
Data in Table 3
Route e Typical Procedure for the Preparation of Amides Via NaCNBH$_3$ Reductive Amination and Acid Chloride Coupling, as Exemplified by the Preparation of Example 11, ethyl 2-{4-fluoro-4-[(1-methylcyclobutyl)carbamoyl]piperidin-1-yl}-6-azaspiro[3.4]octane-6-carboxylate mmol) was added. The reaction mixture was stirred at 50° C., under a nitrogen atmosphere, for 2 h then cooled to rt. NaCNBH$_3$ (0.222 g, 3.54 mmol) was added and the reaction mixture was stirred at 50° C. overnight under nitrogen. The reaction mixture was cooled to rt and the solvents were removed in vacuo, the residue was diluted with DCM and treated with sat. NaHCO$_3$ sol., the resulting heterogeneous mixture was filtered through a celite pad and the filtrate was washed with sat NaHCO$_3$ sol., sat. NaCl sol. and dried over MgSO$_4$. The solvents were removed in vacuo, and the residue was purified by column chromatography (normal phase, [Biotage SNAP cartridge KP-sil 25 g, 40-63 μm, 60 Å, 50 mL per min, gradient 1% to 9% MeOH in DCM]) to give tert-butyl 2-[4-fluoro-4-(methoxycarbonyl)piperidin-1-yl]-6-azaspiro[3.4]octane-6-carboxylate (0.300 g, 46%) as a colourless oil.

LCMS (Method A): m/z 371 (M+H)$^+$ (ES$^+$), at 1.79 and 1.82 min, UV inactive.

Transesterification occurs under these reaction conditions.
tert-Butyl 2-[4-fluoro-4-(methoxycarbonyl)piperidin-1-yl]-6-azaspiro[3.4]octane-6-carboxylate (0.300 g, 0.81 mmol) was dissolved in DCM (4 mL) and TFA (1 mL) was added. The reaction mixture was stirred at rt overnight under nitrogen, then the solvents were removed in vacuo, to give ethyl 1-(6-azaspiro[3.4]oct-2-yl)-4-fluoropiperidine-4-carboxylate trifluoroacetate, as a dark yellow oil which was

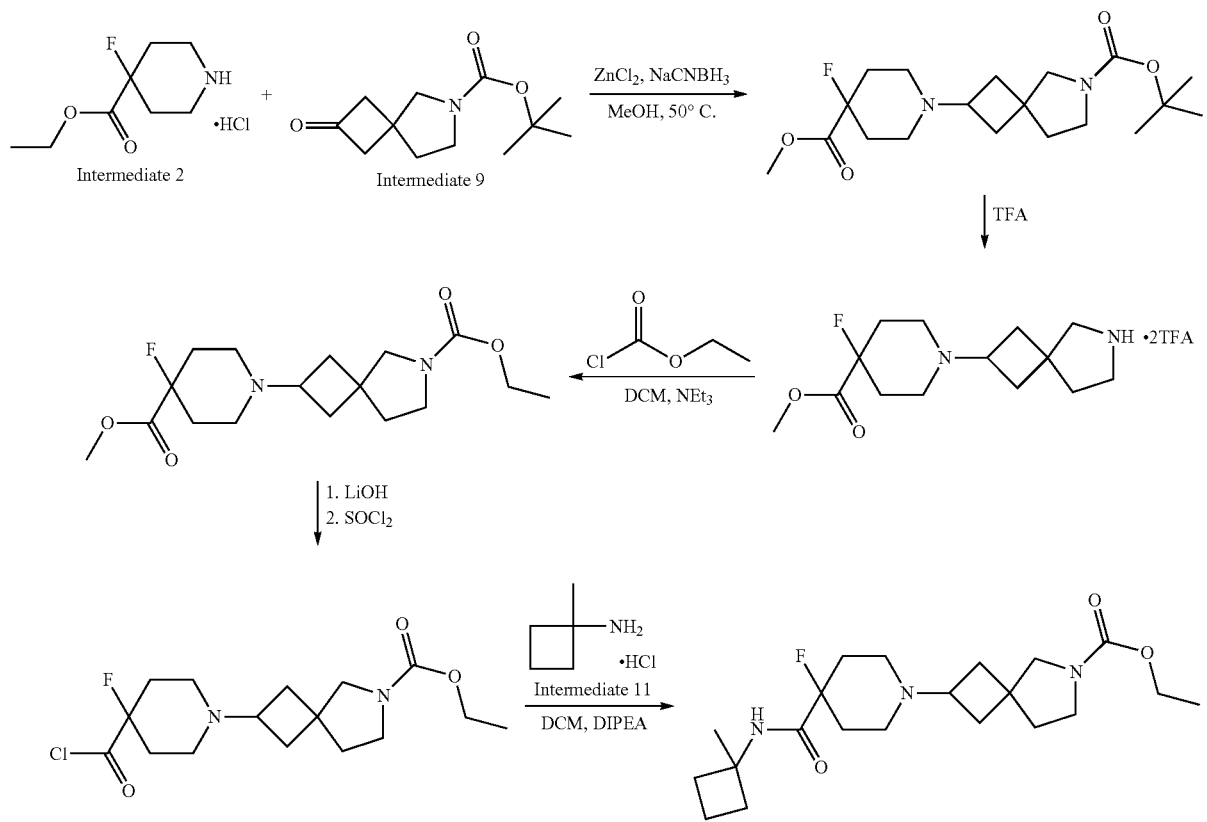

Example 11

Ethyl-4-fluoropiperidine-4-carboxylate hydrochloride (0.376 g, 1.77 mmol) was dissolved in methanol (5 mL) and treated with K$_2$CO$_3$ (0.244 g, 1.77 mmol) in a minimum of water to de-salt. The mixture was concentrated in vacuo and azeotroped to dryness with toluene. The residue was dissolved in methanol (10 mL) and zinc chloride (0.969 g, 7.11 used directly without further purification. The residue was dissolved in DCM (8 mL) at rt. NEt$_3$ (0.246 g, 0.34 mL, 2.43 mmol) and ethyl chloroformate (0.176 g, 0.16 mL, 1.62 mmol) were added and the reaction mixture was stirred at rt overnight under nitrogen. The reaction mixture was partitioned between DCM and sat. NaHCO$_3$ sol., organic layer washed with sat NaCl sol. and dried over MgSO$_4$. The residue was purified by column chromatography (normal phase, [Biotage SNAP cartridge KP-sil 10 g, 40-63 μm, 60 Å, 12 mL per min, gradient 0% to 10% MeOH in DCM]) to give ethyl 2-[4-fluoro-4-(methoxycarbonyl) piperidin-1-yl]-6-azaspiro[3.4]octane-6-carboxylate (0.440 g, 158% impure) as a pale yellow oil.

LCMS (Method A): m/z 343 (M+H)$^+$ (ES$^+$), at 1.56 and 1.59 min, UV inactive.

Ethyl 2-[4-fluoro-4-(methoxycarbonyl) piperidin-1-yl]-6-azaspiro[3.4]octane-6-carboxylate (assumed 0.81 mmol) was dissolved in THF (5 mL) at rt and 1 M LiOH sol. (0.81 mL) was added. The reaction mixture was stirred at rt for 2 days. The pH was carefully adjusted to pH 6 by addition of concentrated hydrochloric acid, the solvents were removed in vacuo, to give 1-[6-(ethoxycarbonyl)-6-azaspiro[3.4]oct-2-yl]-4-fluoropiperidine-4-carboxylic acid as an off white solid, which was used directly without further purification.

LCMS (Method A): m/z 329 (M+H)$^+$ (ES$^+$), at 0.79 and 0.86 min, UV inactive.

Crude 1-[6-(ethoxycarbonyl)-6-azaspiro[3.4]oct-2-yl]-4-fluoropiperidine-4-carboxylic acid was suspended in thionyl chloride (3 mL) and the reaction was stirred at 90° C. for 2 h. The reaction mixture was cooled to rt and concentrated in vacuo. The residue was dissolved in DCM (5 mL) and (1-methylcyclobutyl)amine hydrochloride (0.196 g, 1.62 mmol) and DIPEA (0.523 g, 0.71 mL, 4.05 mmol) were added, the reaction mixture was stirred overnight at rt. The reaction mixture was partitioned between DCM and sat NaHCO$_3$ sol., organic layer washed with sat. NaCl sol. and dried over MgSO$_4$. The residue was purified by column chromatography (normal phase, [Biotage SNAP cartridge KP-sil 25 g, 40-63 μm, 60 Å, 12 mL per min, gradient 0% to 6% MeOH in DCM]) to give ethyl 2-{4-fluoro-4-[(1-methylcyclobutyl)carbamoyl]piperidin-1-yl)}-azaspiro[3.4]octane-6-carboxylate (0.09 g, 28%) as a pale yellow gum as a mixture of diastereomers.

Data in Table 3

Route f

Typical Procedure for the Preparation of Amides, Followed by Chloroformate Coupling, as Exemplified by the Preparation of Example 14, ethyl 2-[4-(tert-butylcarbamoyl) piperidin-1-yl]-6-azaspiro[3.4]octane-6-carboxylate Ethyl piperidine-4-carboxylate (0.35 g, 0.32 mL, 2.22 mmol) and 6-azaspiro[3.4]octane-6-carboxylic acid, 2-oxo-, 1,1-dimethylethyl ester (0.500 g, 2.22 mmol) were dissolved in DCM (20 mL) at rt and titanium isopropoxide (4.12 g, 4.40 mL, 14.5 mmol) was added. The reaction mixture was stirred at rt for 1 h. STAB (0.694 g, 0.72 mL, 2.44 mmol) and acetic acid (0.05 mL) were added and the reaction mixture was stirred at rt overnight under nitrogen. The reaction mixture was quenched with the addition of sat. NaHCO$_3$ sol (5 mL) and stirred for 5 minutes. The reaction mixture was diluted with DCM and filtered through a pad of celite. The filtrate was separated and washed with sat. NaCl sol. and dried over MgSO$_4$. The solvents were removed in vacuo, and the residue was purified by column chromatography (normal phase, [Biotage SNAP cartridge KP-sil 50 g, 40-63 tam, 60 Å, 50 mL per min, gradient 0% to 5% MeOH in DCM]) to give tert-butyl 2-[4-(ethoxycarbonyl)piperidin-1-yl]-6-azaspiro[3.4]octane-6-carboxylate (0.739 g, 90.9%) as a pale yellow oil.

LCMS (Method A): m/z 367 (M+H)$^+$ (ES$^+$), at 1.94/1.99 min, UV inactive tert-Butyl 2-[4-(ethoxycarbonyl)piperidin-1-yl]-6-azaspiro[3.4]octane-6-carboxylate (0.739 g, 2.02 mmol) was dissolved in THF (10 mL) at rt and 1 M LiOH sol. (2.02 mL) was added. The reaction mixture was stirred at rt overnight. The reaction mixture was adjusted to pH 5 by addition of 1 M HCl sol. and solvents were removed in vacuo, to give 1-[6-(tert-butoxycarbonyl)-6-azaspiro[3.4]oct-2-yl]piperidine-4-carboxylic acid, which was used crude in the subsequent reaction.

LCMS (Method A): m/z 339 (M+H)$^+$ (ES$^+$), at 0.12 min, UV inactive

1-[6-(tert-Butoxycarbonyl)-6-azaspiro[3.4]oct-2-yl]piperidine-4-carboxylic acid was dissolved in DMF (2 mL) and t-butylamine (0.087 g, 1.20 mmol), HATU (0.227 g, 0.60 mmol) and DIPEA (0.193 g, 1.50 mmol) were added. The reaction mixture was stirred at rt overnight under nitrogen. The solvents were removed in vacuo, and the residue was partitioned between DCM and sat. NaHCO$_3$ sol., organic layer washed with sat. NaCl sol. and dried over MgSO$_4$. The solvents were removed in vacuo, and the residue was

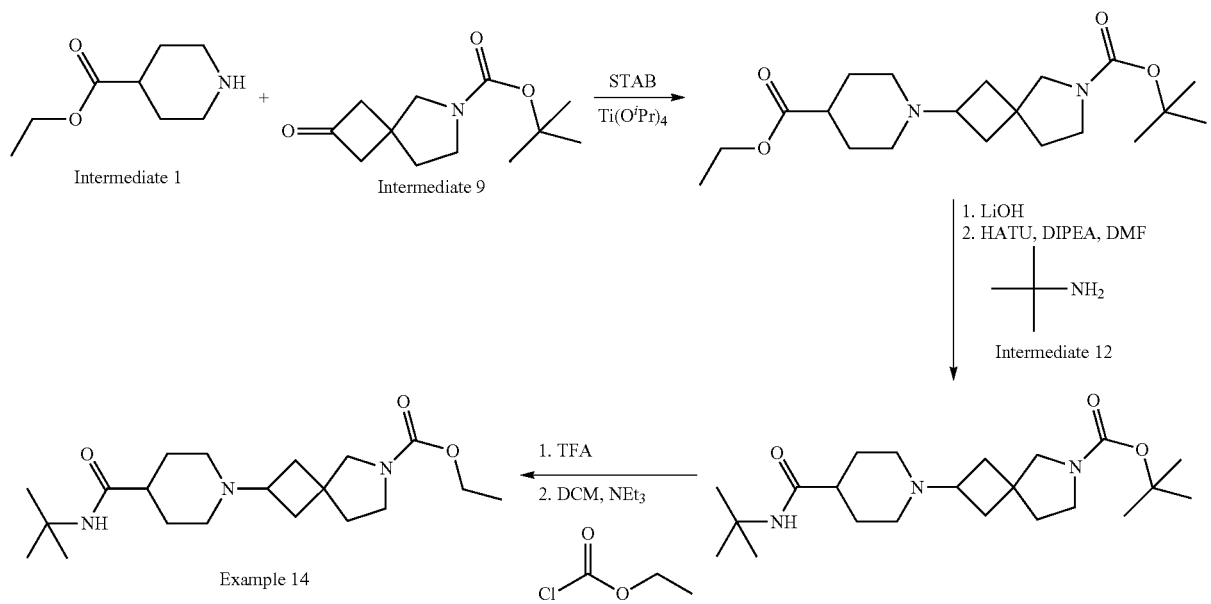

purified by column chromatography (normal phase, [Biotage SNAP cartridge KP-sil 10 g, 40-63 μm, 60 Å, 12 mL per min, gradient 0% to 10% MeOH in DCM]) to give tert-butyl-2-[4-(tert-butylcarbamoyl)piperidin-1-yl]-6-azaspiro[3.4]octane-6-carboxylate (0.071 g, 60.5%) as a yellow oil.

LCMS (Method A): m/z 394 (M+H)$^+$ (ES$^+$), at 1.79 min, UV inactive tert-Butyl-2-[4-(tert-butylcarbamoyl)piperidin-1-yl]-6-azaspiro[3.4]octane-6-carboxylate (0.627 g, 1.55 mmol) was dissolved in DCM (4 mL) and TFA (1 mL) was added. The reaction mixture was stirred at rt overnight under nitrogen, then the solvents were removed in vacuo, to give 1-(6-azaspiro[3.4]oct-2-yl)-N-tert-butylpiperidine-4-carboxamide trifluoroacetate (1:2) as an oil which was used directly without further purification. The residue was dissolved in DCM (8 mL) and NEt$_3$ (0.056 g, 0.08 mL, 0.54 mmol) and ethyl chloroformate (0.024 mg, 0.02 mL, 0.22 mmol) were added and the reaction mixture was stirred at rt overnight under nitrogen. The solvents were removed in vacuo, and the residue was partitioned between DCM and sat. NaHCO$_3$ sol., organic layer washed with sat. NaCl sol. and dried over MgSO$_4$. The residue was purified by column chromatography (normal phase, [Biotage SNAP cartridge KP-sil 10 g, 40-63 μm, 60 Å, 12 mL per min, gradient 0% to 10% MeOH in DCM]) to give ethyl 2-[4-(tert-butylcarbamoyl)piperidin-1-yl]-6-azaspiro[3.4]octane-6-carboxylate (0.027 g, 41%) as an off-white solid as a mixture of diastereomers.
Data in Table 3
Route a Alternative Procedure for the Preparation of Carbamates Via Amide Coupling, as Exemplified by the Preparation of Example 13, ethyl 2-{4-[(2-methylpropyl)carbamoyl]piperidin-1-yl}-6-azaspiro[3.4]octane-6-carboxylate was stirred at rt overnight under nitrogen. The reaction mixture was quenched with the addition of sat. NaHCO$_3$ sol (5 mL) and stirred for 5 minutes. The reaction mixture was diluted with DCM and filtered through a pad of celite. The filtrate was separated and washed with sat. NaCl sol. and dried over MgSO$_4$. The solvents were removed in vacuo, and the residue was purified by column chromatography (normal phase, [Biotage SNAP cartridge KP-sil 50 g, 40-63 μm, 60 Å, 50 mL per min, gradient 0% to 5% MeOH in DCM]) to give tert-butyl 2-[4-(ethoxycarbonyl)piperidin-1-yl]-6-azaspiro[3.4]octane-6-carboxylate (0.739 g, 90.9%) as a pale yellow oil.

LCMS (Method A): m/z 367 (M+H)$^+$ (ES$^+$), at 1.94/1.99 min, UV inactive tert-Butyl 2-[4-(ethoxycarbonyl)piperidin-1-yl]-6-azaspiro[3.4]octane-6-carboxylate (3.00 g, 8.20 mmol) was dissolved in DCM (40 mL) and stirred with 4 M HCl in Dioxan (10 mL) at rt overnight. The reaction mixture was conc. in vacuo to give ethyl 1-(6-azaspiro[3.4]oct-2-yl)piperidine-4-carboxylate trifluoroacetate (1:2) as a pale pink solid which was used in the next step without further purification. Ethyl 1-(6-azaspiro[3.4]oct-2-yl)piperidine-4-carboxylate trifluoroacetate (1:2) residue was dissolved in DCM (40 mL) and NEt$_3$ (2.49 g, 3.42 mL, 24.6 mmol) and ethyl chloroformate (1.07 g, 0.93 mL, 9.84 mmol) were added and the reaction mixture was stirred at rt overnight under nitrogen. The solvents were removed in vacuo, and the residue was partitioned between DCM and sat NaHCO$_3$ sol., organic layer washed with sat. NaCl sol. and dried over MgSO$_4$. The residue was purified by column chromatography (normal phase, [Biotage SNAP cartridge KP-sil 50 g, 40-63 μm, 60 Å, 50 mL per min, gradient 0% to 10% MeOH in DCM]) to give ethyl 2-[4-(ethoxycarbonyl)piperidin-1-yl]-6-azaspiro[3.4]octane-6-carboxylate (2.474 g, 89%) as an orange oil.

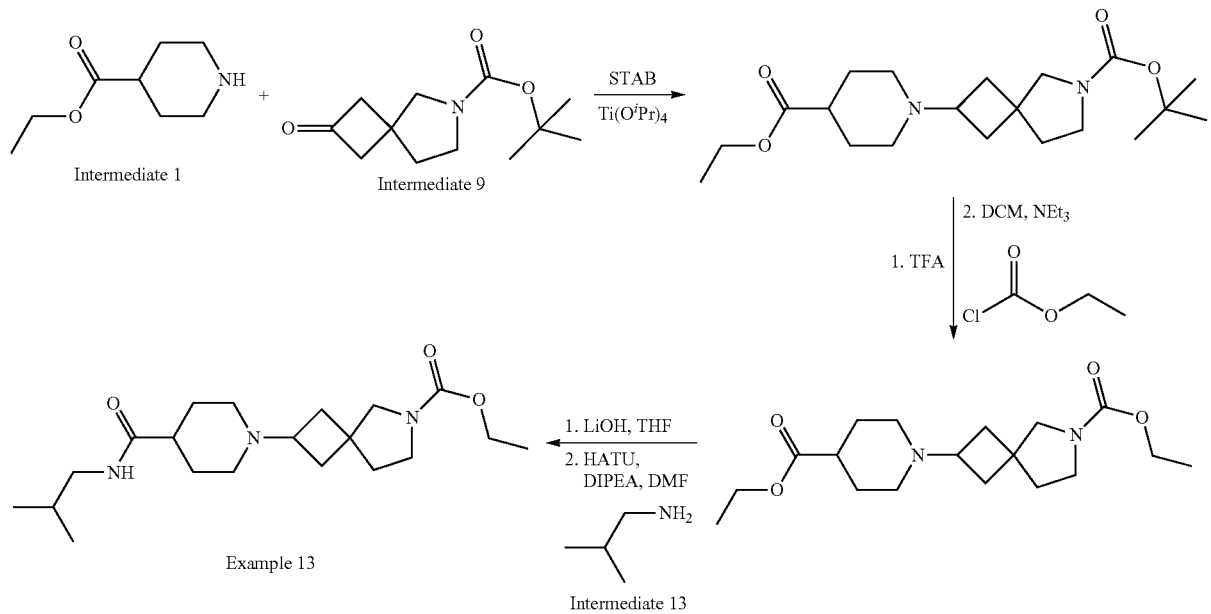

Ethyl piperidine-4-carboxylate (0.35 g, 0.32 mL, 2.22 mmol) and 6 azaspiro[3.4]octane-6-carboxylic acid, 2-oxo-, 1,1-dimethylethyl ester (0.500 g, 2.22 mmol) were dissolved in DCM (20 mL) at rt and titanium isopropoxide (4.12 g, 4.40 mL, 14.5 mmol) was added. The reaction mixture was stirred at rt for 1 h. STAB (0.694 g, 0.72 mL, 2.44 mmol) and acetic acid (0.05 mL) were added and the reaction mixture LCMS (Method A): m/z 339 (M+H)$^+$ (ES$^+$), at 1.67/1.71 min, UV inactive.

Ethyl 2-[4-(ethoxycarbonyl)piperidin-1-yl]-6-azaspiro [3.4]octane-6-carboxylate (2.474 g, 7.32 mmol) was dissolved in THF (25 mL) at rt and 1 M LiOH sol. (7.32 mL) was added. The reaction mixture was stirred at rt over the weekend. The reaction mixture was adjusted to pH 5 by addition of 1 M HCl sol. and solvents were removed in vacuo, to give 1-[6-(ethoxycarbonyl)-6-azaspiro[3.4]oct-2-yl]piperidine-4-carboxylic acid which was used directly without further purification.

LCMS (Method A): m/z 311 (M+H)$^+$ (ES$^+$), at 0.85/0.91 min, UV inactive.

1-[6-(Ethoxycarbonyl)-6-azaspiro[3.4]oct-2-yl]piperidine-4-carboxylic acid (0.200 g, 0.65 mmol) was dissolved in DMF (5 mL) isobutylamine (0.071 g, 0.97 mmol), HATU (0.270 g, 0.71 mmol) and DIPEA (0.417 g, 3.23 mmol) were added. The reaction mixture was stirred at rt overnight under nitrogen. The solvents were removed in vacuo, and the residue was partitioned between DCM and sat. NaHCO$_3$ sol., organic layer washed with sat. NaCl sol. and dried over MgSO$_4$. The solvents were removed in vacuo, and the residue was purified by column chromatography (normal phase, [Biotage SNAP cartridge KP-sil 25 g, 40-63 µm, 60 Å, 12 mL per min, gradient 0% to 10% MeOH in DCM]) to give ethyl 2-{4-[(2-methylpropyl)carbamoyl]piperidin-1-yl}-6-azaspiro[3.4]octane-6-carboxylate (0.089 g, 37.7%) as a pale yellow gum as a mixture of diastereomers.
Data in Table 3
Route h
Alternative Procedure for the Preparation of Carbamates Via Para-Nitro Phenylcarbamate Activation, as Exemplified by the Preparation of Example 25, (2,2,2-trideutero)ethyl 2-{4-[(1-methylcyclobutyl)carbamoyl]piperidin-1-yl}-6-azaspiro[3.4]octane-6-carboxylate Ethyl piperidine-4-carboxylate (0.35 g, 0.32 mL, 2.22 mmol) and 6 azaspiro[3.4]octane-6-carboxylic acid, 2-oxo-, 1,1-dimethylethyl ester (0.500 g, 2.22 mmol) were dissolved in DCM (20 mL) at rt and titanium isopropoxide (4.12 g, 4.40 mL, 14.5 mmol) was added. The reaction mixture was stirred at rt for 1 h. STAB (0.694 g, 0.72 mL, 2.44 mmol) and acetic acid (0.05 mL) were added and the reaction mixture was stirred at rt overnight under nitrogen. The reaction mixture was quenched with the addition of sat. NaHCO$_3$ sol (5 mL) and stirred for 5 minutes. The reaction mixture was diluted with DCM and filtered through a pad of celite. The filtrate was separated and washed with sat. NaCl sol. and dried over MgSO$_4$. The solvents were removed in vacuo, and the residue was purified by column chromatography (normal phase, [Biotage SNAP cartridge KP-sil 50 g, 40-63 µm, 60 Å, 50 mL per min, gradient 0% to 5% MeOH in DCM]) to give tert-butyl 2-[4-(ethoxycarbonyl)piperidin-1-yl]-6-azaspiro[3.4]octane-6-carboxylate (0.739 g, 90.9%) as a pale yellow oil.

LCMS (Method A): m/z 367 (M+H)$^+$ (ES$^+$), at 1.94/1.99 min, UV inactive tert-Butyl 2-[4-(ethoxycarbonyl)piperidin-1-yl]-6-azaspiro[3.4]octane-6-carboxylate (0.739 g, 2.02 mmol) was dissolved in THF (10 mL) at rt and 1 M LiOH sol. (2.02 mL) was added. The reaction mixture was stirred at rt overnight. The reaction mixture was adjusted to pH 5 by addition of 1 M HCl sol. and solvents were removed in vacuo, to give 1-[6-(tert-butoxycarbonyl)-6-azaspiro[3.4]oct-2-yl]piperidine-4-carboxylic acid, which was used crude in the subsequent reaction.

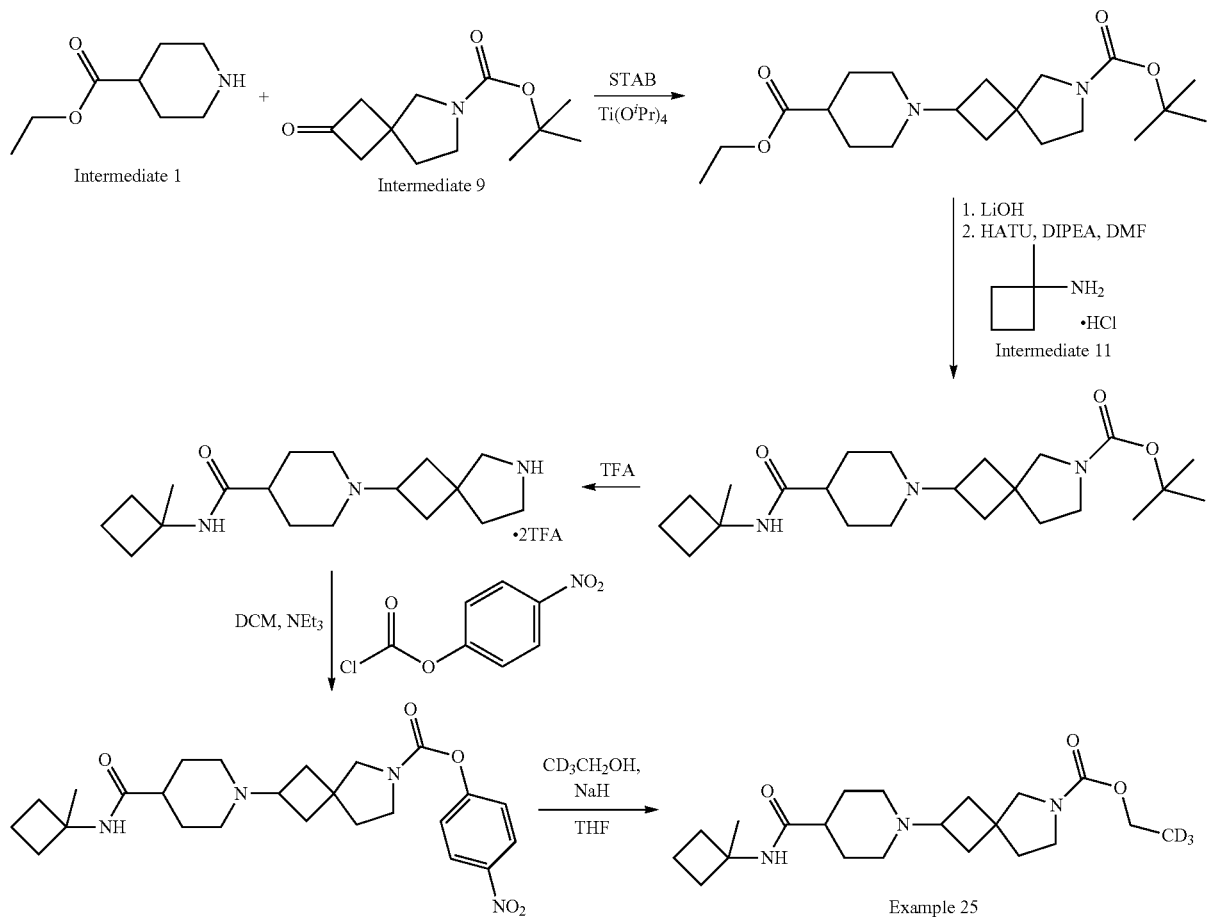

LCMS (Method A): m/z 339 (M+H)+ (ES+), at 0.12 min, UV inactive

1-[6-(tert-Butoxycarbonyl)-6-azaspiro[3.4]oct-2-yl]piperidine-4-carboxylic acid was dissolved in DMF (5 mL) and (1-methylcyclobutyl)amine hydrochloride (0.37 g, 3.03 mmol), HATU (0.844 g, 2.22 mmol) and DIPEA (1.305 g, 10.1 mmol) were added. The reaction mixture was stirred at rt overnight under nitrogen. The solvents were removed in vacuo, and the residue was partitioned between DCM and sat. NaHCO₃ sol., organic layer washed with sat. NaCl sol. and dried over MgSO₄. The solvents were removed in vacuo, and the residue was purified by column chromatography (normal phase, [Biotage SNAP cartridge KP-sil 50 g, 40-63 μm, 60 Å, 50 mL per min, gradient 0% to 10% MeOH in DCM]) to give tert-butyl 2-{4-[(1-methylcyclobutyl)carbamoyl]piperidin-1-yl}-6-azaspiro[3.4]octane-6-carboxylate (0.627 g, 76.7%) as a white foam.

LCMS (Method A): m/z 406 (M+H)+ (ES+), at 1.81 min, UV inactive tert-Butyl 2-{4-[(1-methylcyclobutyl)carbamoyl]piperidin-1-yl}-6-azaspiro[3.4]octane-6-carboxylate (0.747 g, 1.84 mmol) was dissolved in DCM (8 mL) and TFA (2 mL) was added. The reaction mixture was stirred at rt overnight under nitrogen, then the solvents were removed in vacuo, to give 1-(6-azaspiro[3.4]oct-2-yl)-N-(1-methylcyclobutyl)piperidine-4-carboxamide trifluoroacetate as a dark yellow oil which was used directly without further purification. The residue was dissolved in DCM (10 mL) and NEt₃ (0.56 g, 0.77 mL, 5.52 mmol) and 4-nitrophenyl chloroformate (0.555 g, 2.76 mmol) were added and the reaction mixture was stirred at rt overnight under nitrogen. The solvents were removed in vacuo, and the residue was partitioned between DCM (15 mL) and 1 N NaOH sol. (15 mL). The aqueous layer was extracted with DCM (4×20 mL), dried over MgSO₄ and the solvent evaporated. The residue was semi-purified by column chromatography (normal phase, [Biotage SNAP cartridge KP-sil 25 g, 40-63 μm, 60 Å, 25 mL per min, gradient 0% to 10% MeOH in DCM]) to give 4-nitrophenyl 2-{4-[(1-methylcyclobutyl)carbamoyl]piperidin-1-yl}-6-azaspiro[3.4]octane-6-carboxylate (0.60 g, 69%) as a yellow gum as a mixture of diastereomers.

LCMS (Method C): m/z 471 (M+H)+ (ES+), at 4.60 min, UV active.

Ethanol-2,2,2-d3 (0.186 g, 0.22 mL, 3.78 mmol) was dissolved in THF (12.6 mL) and cooled 0° C. Sodium hydride (0.202 g, 5.044 mmol) was added and stirred for 1 h. 4-Nitrophenyl 2-{4-[(1-methylcyclobutyl)carbamoyl]piperidin-1-yl}-6-azaspiro[3.4]octane-6-carboxylate (0.600 g, 1.26 mmol) dissolved in THF (12.6 mL) was added and the mixture stirred overnight under nitrogen. The mixture was partitioned between EtOAc (30 mL) and water (30 mL). The aqueous layer was extracted with EtOAc (4×30 mL), dried over MgSO₄ and the solvent evaporated. The residue was semi-purified by column chromatography (normal phase, [Biotage SNAP cartridge KP-sil 25 g, 40-63 μm, 60 Å, 25 mL per min, gradient 0% to 10% MeOH in DCM]) to give ethyl-2,2,2-d3 2-{4-[(1-methylcyclobutyl)carbamoyl]piperidin-1-yl}-6-azaspiro[3.4]octane-6-carboxylate (0.240 g, 50%) as a yellow gum as a mixture of diastereomers. Separation of diastereomers was achieved via preparative HPLC to give (2,2,2-trideutero)ethyl 2-{4-[(1-methylcyclobutyl)carbamoyl]piperidin-1-yl}-6-azaspiro[3.4]octane-6-carboxylate isomer 1 (0.094 g, 39%) as an off-white gum and isomer 2 (0.085 g, 35%) as an off-white gum.

Data in Table 3

Synthesis of Intermediates

Route i

Typical Procedure for the Preparation of Amines, as Exemplified by the Preparation of Intermediate 19, 1-(1,1,1-trideuteromethyl) cyclobutan-1-amine hydrochloride

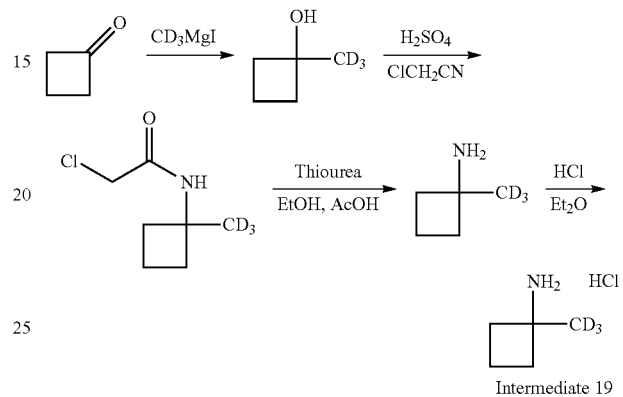

Intermediate 19

Magnesium (2.67 g, 110 mmol) was stirred in dry ether in a three necked flask fitted with a thermometer and dropping funnel. 1,1,1-Trideuteromethyl iodide (6.24 mL, 100 mmol) in diethyl ether (40 mL) was charged to the dropping funnel and a small crystal of iodine added to the magnesium suspension. The magnesium suspension was warmed briefly until the iodine colouration dissipated then the 1,1,1-trideuteromethyl iodide solution added drop-wise (causing a small exotherm). Once the addition was complete, the mixture was warmed to 32° C. for 30 mins then cooled to 0° C. Cyclobutanone (5 mL, 67 mmol) was dissolved in diethyl ether (20 mL), dried over magnesium sulfate and filtered. The solution was added drop-wise to the reaction mixture, keeping the temperature<15° C., then allowed to reach room temperature overnight. The mixture was partitioned between aqueous ammonium chloride (100 mL) and diethyl ether (100 mL) and extracted 4 more times with ether. The organic layer was dried over sodium sulfate and concentrated (250 mbar, 40° C.) to give a yellow oil (5.9 g, 75%).

¹H NMR (300 MHz, CDCl₃) δ: 1.41-1.52 (1H, m), 1.60-1.81 (2H, m), 1.95-2.06 (4H, m).

Chloroacetonitrile (21.6 mL, 340 mmol) was added to a solution of 1-(1,1,1-trideuteromethyl)cyclobutan-1-ol (10.14 g, 113.7 mmol) and acetic acid (3.1 mL). The mixture was cooled to 0° C. and concentrated sulfuric acid (18.3 mL) was added dropwise. Once the addition was complete the solution was allowed to reach room temperature and stirred for 2 hours. The reaction was poured into ice/water (200 mL) and extracted with dichloromethane (3×150 mL). The organic layers were combined, washed with aqueous sodium carbonate solution (100 mL) and brine (100 mL), dried over sodium sulfate and concentrated to give a yellow oil. This oil was azeotroped with toluene to give a beige solid (19.7 g, 105%) which was used directly without purification.

¹H NMR (300 MHz, CDCl₃) δ: 1.79-1.90 (2H, m), 1.99-2.06 (2H, m), 2.23-2.32 (2H, m), 3.94 (2H, s), 6.59 (1H, bs).

A solution of 2-chloro-N-(1-(1,1,1-trideuteromethyl)cyclobutyl)acetamide (10 g, 60.7 mmol) and thiourea (5.69 g, 74.8 mmol) in ethanol (45 mL) and acetic acid (6.1 mL) was refluxed overnight. The reaction mixture was allowed to cool to room temperature and concentrated to approximately 22 mL. The mixture was added to water (45 mL) and filtered to remove the precipitate. The filtrate was washed with diethyl ether (100 mL, discarded) then basified with NaOH (aq) to pH 13. The basic layer was extracted with dichloromethane (4×100 mL), combined & dried over sodium sulfate and concentrated (200 mbar, 40° C.) to give a yellow oil (2.08 g). The oil was dissolved in diethyl ether (80 mL) and stirred whilst HCl in diethyl ether (17 mL, 2 M) was added dropwise. The resulting precipitate was filtered, washed with diethyl ether then dried under vacuum at 40° C. to give 1-(1,1,1-trideuteromethyl) cyclobutan-1-amine hydrochloride (2.35 g, 31%).

$^1$H NMR (300 MHz, D$_2$O) δ: 1.79-1.89 (2H, m), 1.98-2.03 (2H, m), 2.15-2.25 (2H, m).

$^{13}$C NMR (300 MHz, D$_2$O) δ: 13.0, 22.5 (m), 32.0, 54.0.

Route j

Typical Procedure for the Preparation of Amines, as Exemplified by the Preparation of Intermediate 20, 1-(fluoromethyl)cyclobutan-1-amine hydrochloride

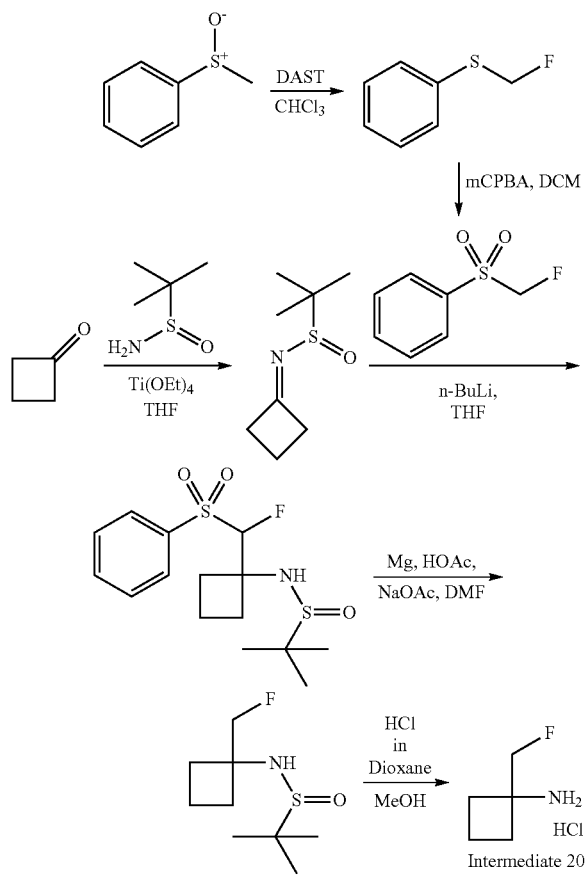

To a stirred solution of (methylsulfinyl)benzene (23.0 g, 164 mmol) in chloroform (80 mL) under argon at room temperature was added diethylaminosulfur trifluoride (43.0 mL, 328 mmol) dropwise and the reaction mixture was stirred for 2 days at this temperature then at 60° C. overnight. The mixture was added dropwise to a stirred solution of saturated aqueous sodium hydrogen carbonate at 0° C. then extracted 3 times with dichloromethane. The combined organic layers were dried over sodium sulfate and concentrated to give (fluoromethyl)(phenyl)sulfane (20.0 g, 86%) as a yellow oil.

$^1$H NMR (300 MHz, CDCl$_3$) δ: 5.64 (s, 1H), 5.81 (s, 1H), 7.38-7.24 (m, 3H), 7.53-7.46 (m, 2H).

To a stirred solution of (fluoromethyl)(phenyl)sulfane (20.0 g, 140 mmol) in dichloromethane (300 mL) was added meta-chloroperoxybenzoic acid (84.0 g, 475 mmol) potionwise at 0° C. The reaction mixture was allowed to warm slowly to room temperature and stirred overnight. The mixture was poured into a stirred solution of saturated aqueous sodium hydrogen carbonate at 0° C., then extracted three times with dichloromethane. The combined organic layers were washed brine, dried over sodium sulfate and concentrated to give a yellow oil. The residue was purified by flash column chromatography on silica (eluent heptane:ethyl acetate, 9:1 to 4:1) to give ((fluoromethyl)sulfonyl)benzene (22.9 g, 93%) as a yellow oil.

$^1$H NMR (300 MHz, CDCl$_3$) δ: 5.05 (s, 1H), 7.63 (t, 2H), 7.73 (t, 1H), 7.97 (d, 2H).

A mixture of titanium (IV) ethoxide (22.4 mL, 107 mmol) and cyclobutanone (5.37 mL, 71.0 mmoL) in tetrahydrofuran (120 mL) was stirred for 10 minutes. Tert-butanesulfinamide (7.17 g, 59.0 mmol) was added and the reaction mixture was stirred at room temperature for 18 hours. The mixture was concentrated and the residue dissolved in ethyl acetate. The solution was washed with saturated aqueous sodium hydrogen carbonate, dried over sodium sulphate and concentrated to give N-cyclobutylidene-2-methylpropane-2-sulfinamide (9.51 g, 77%) as a pale yellow oil which was used directly without purification.

$^1$H NMR (300 MHz, CDCl$_3$) δ: 1.18 (s, 9H), 2.12-1.97 (m, 2H), 3.10-3.00 (m, 2H), 3.29-3.11 (m, 1H), 3.52-3.37 (m, 1H).

LCMS (Method D): m/z 174 (M+H)$^+$ (ES$^+$), at 1.10 min.

To a stirred solution of ((fluoromethyl)sulfonyl)benzene (5.0 g, 28.7 mmol) in tetrahydrofuran (100 mL) at −78° C. under argon was added n-butyl lithium (18.0 mL, 28.7 mmol) and the reaction mixture was stirred for 40 minutes at this temperature. N-cyclobutylidene-2-methylpropane-2-sulfinamide (3.23 g, 18.7 mmol) was added to the mixture at −78° C. and the reaction mixture was allowed to warm slowly to room temperature and stirred overnight. The reaction mixture was quenched by the addition of water and extracted 3 times with dichloromethane. The combined organic layers were washed with brine, dried over sodium sulfate and concentrated to afford a brown oil. The residue was purified by flash column chromatography on silica (eluent heptane:ethyl acetate, 3:2 to 2:3) to give N-(1-(fluoro(phenylsulfonyl)methyl)cyclobutyl)-2-methylpropane-2-sulfinamide (3.00 g, 33%) as a yellow oil.

$^1$H NMR (300 MHz, CDCl$_3$) δ: 1.27 (s, 9H), 1.96-1.82 (m, 1H), 2.14-2.00 (m, 2H), 2.38-2.26 (m, 1H), 2.59-2.43 (m, 1H), 2.91-2.76 (m, 1H), 5.04 (s, 1H), 5.53-5.55 (m, 1H), 7.52-7.55 (m, 2H), 7.62-7.65 (m, 1H), 7.93-7.95 (m, 2H).

LCMS (Method D): m/z 348 (M+H)$^+$ (ES$^+$), at 1.54 min.

To a stirred solution of N-(1-(fluoro(phenylsulfonyl)methyl)cyclobutyl)-2-methylpropane-2-sulfinamide (1.50 g, 4.32 mmol) in N,N-dimethylformamide (270 mL) was added a buffer solution of sodium acetate (22.6 g, 276 mmol) in acetic acid (34.6 mL) and the reaction mixture was stirred for 15 minutes at room temperature. Magnesium turnings (6.92 g, 289 mmol) were added and the mixture stirred at 65° C. for 24 hours. The mixture was treated with water and saturated aqueous sodium hydrogen carbonate and extracted 3 times with ethyl acetate. The combined organic layer was dried over sodium sulfate and concentrated to give a yellow oil. The residue was purified by flash column chromatography on silica (eluent: heptane:ethyl acetate 1:1 to 0:1) to give N-(1-(fluoromethyl)cyclobutyl)-2-methylpropane-2-sulfinamide (560 mg, 53%) as a pale yellow oil.

$^1$H NMR (300 MHz, CDCl$_3$) δ: 1.20 (s, 9H), 1.99-1.68 (m, 2H), 3.62 (br s, 1H), 4.36-4.38 (m, 1H), 4.52-4.54 (m, 1H).

To a stirred solution of N-(1-(fluoromethyl)cyclobutyl)-2-methylpropane-2-sulfinamide (1.50 g, 7.23 mmol) in methanol (20 mL) was added hydrochloric acid (20 mL, 7.23 mmol, 4 M in dioxane) at 0° C. under argon and the reaction mixture was allowed to warm to room temperature and stir for 1 hour. The mixture was concentrated and the crude product triturated in diethyl ether and tert-butyl methyl ether to give the desired product 1-(fluoromethyl)cyclobutan-1-amine hydrochloride (0.90 g, 90%).

$^1$H NMR (300 MHz, CDCl$_3$) δ: 1.92-1.76 (m, 2H), 2.09-1.93 (m, 2H), 2.36-2.16 (m, 2H), 4.54 (s, 1H), 4.70 (s, 1H), 8.68 (br s, 2H).

LCMS (Method D): m/z 104 (M+H)$^+$ (ES$^+$), at 1.31 min.

Route k

Typical Procedure for the Preparation of Amines, as Exemplified by the Preparation of Intermediate 21, 1-(1,1,1-trideuteromethyl)-2,2,3,3,4,4-hexadeuterocyclobutan-1-amine hydrochloride ture below 35° C. and the reaction mixture was stirred at room temperature overnight. Water (40 mL) was added cautiously followed by sodium hydroxide (40 mL, 15% aqueous solution), then further water (120 mL) and the mixture was stirred at room temperature overnight. The mixture was filtered through celite washing with tetrahydrofuran:methanol (1:3, 1.0 L) and the filtrate was concentrated to give a crude residue (76.0 g). The aluminium salts were suspended in ethyl acetate:methanol (2:1, 3.0 L), stirred for 1 hour, filtered and the filtrate concentrated to give a further crop of crude residue (126 g). The two residues were combined and purified by distillation to give the desired product 1,1,2,2,3,3-hexadeuterio-propane-1,3-diol (56.0 g, 57%).

$^{13}$C NMR (300 MHz, CDCl$_3$) δ: 35.1, 57.6, 171.0

GC (Method F): 20 min, at 10.96 min, 99.22%.

The reaction was carried out in 2 batches. N-bromosuccinimide (196 g, 1.10 mol) was added portionwise to a solution of 1,1,2,2,3,3-hexadeuterio-propane-1,3-diol (28.0 g, 0.368 mol) and triphenyl phosphine (289 g, 1.10 mol) in acetonitrile (500 mL) and dichloromethane (500 mL) keeping the temperature below 35° C. The reaction mixture was stirred at room temperature overnight. Hexane (1 L) was added and the layers separated and re-extracted with hexane (400 mL). The combined hexane layers were washed with sodium hydroxide (250 mL, 2 M), then saturated aqueous sodium sulfite (200 mL), brine (200 mL), dried over magnesium sulfate and concentrated. The residue was triturated

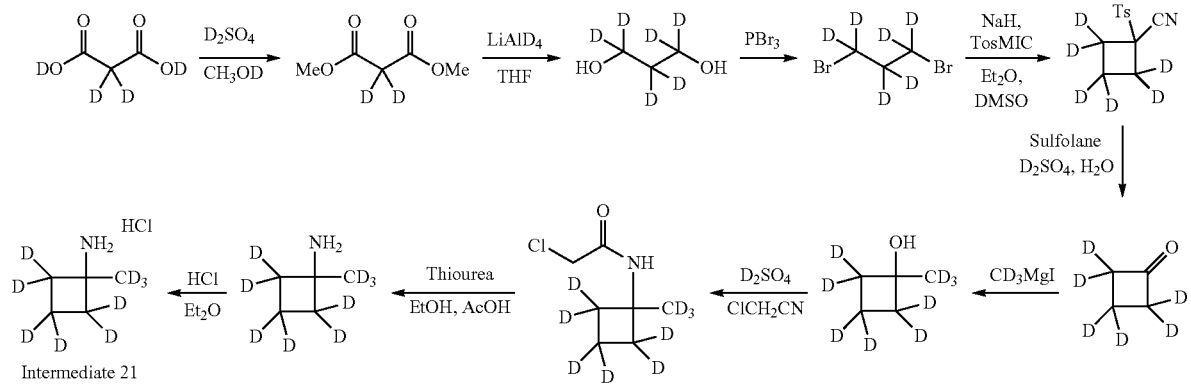

Malonic acid-d4 (165 g, 1.53 mol), sulfuric acid-d2 (5.0 mL) and methan(ol-d) (330 mL) in dichloromethane (825 mL) were stirred at room temperature for 4 days. Deuterium oxide (100 mL) was added and the phases separated. The aqueous phase was re-extracted with dichloromethane (100 mL). The combined organic phases were dried over sodium sulfate and concentrated to give a colourless oil. The residue was purified by distillation (bp: 105° C. at 25 mmHg) to give the desired product 2,2-dideuterio-malonic acid dimethyl ester (161 g, 79%) as a colourless oil.

$^1$H NMR (300 MHz, CDCl$_3$) δ: 3.76 (s, 6H).

$^{13}$C NMR (300 MHz, CDCl$_3$) δ: 40.7, 52.6, 167.0.

GC (Method F): 20 min, at 11.91 min, 99.65%.

The reaction was carried out in 2 batches of 80.5 g. Lithium aluminium deuteride (40.0 g, 0.90 mol) was added portionwise to anhydrous tetrahydrofuran (1.0 L) under argon and cooled to 0° C. 2,2-Dideuterio-malonic acid dimethyl ester (80.5 g, 0.60 mol) in anhydrous tetrahydrofuran (300 mL) was added slowly maintaining the temperawith heptane and the solid removed by filtration. The filtrate was concentrated and the residue triturated a second time with heptane. The solid was removed by filtration and the filtrates from each batch concentrated to give crude product (44.0 g and 34.0 g respectively). The combined residues were purified by distillation to give 1,1,2,2,3,3-hexadeuterio-1,3-dibromopropane (44.0 g, 62%).

GC (Method F): 20 min, at 12.10 min, 73.71%.

To a cooled suspension of sodium hydride (20.3 g, 508 mmol, 60% dispersion in oil) in dimethylsulfoxide (450 mL) and diethyl ether (110 mL) was added a solution of 1,1,2,2,3,3-hexadeuterio-1,3-dibromopropane (44.0 g, 213 mmol) and p-toluenesulfonylmethyl isocyanide (33.4 g, 171 mmol) in dimethylsulfoxide (100 mL) and diethyl ether (25 mL) dropwise. The reaction mixture was stirred at 0° C. for 15 minutes then warmed to room temperature for 1 hour. During this time a solid precipitated and the reaction mixture had set solid. Dimethylsulfoxide (200 mL) was added, the solid broken up and the mixture stirred for 3 hours. Water (500 mL) was added cautiously, the solid was collected by filtration and dried to give 1-((1-isocyano-2,2,3,3,4,4-hexadeuterocyclobutane)sulfonyl)-4-methylbenzene (41.6 g, 80%) as a brown solid. Which was used without further purification.

$^1$H NMR (400 MHz, CDCl$_3$) δ: 2.46 (s, 3H), 7.38-7.42 (m, 2H), 7.83-7.86 (m, 2H).

$^{13}$C NMR (300 MHz, CDCl$_3$) δ: 14.2, 21.9, 30.8, 73.9, 129.9, 130.6, 146.5, 164.88.

To a solution of 1-((1-isocyano-2,2,3,3,4,4-hexadeuterocyclobutane)sulfonyl)-4-methylbenzene (41.6 g, 172 mmol) in distilled sulfolane (120 mL) was added a cooled mixture of sulfuric acid-d2 (9.4 mL) and deuterium oxide (9.4 mL) in one portion. The reaction mixture was subjected to high vacuum (using potassium carbonate and potassium hydroxide traps) and heated to 120° C. The product was collected in a cold finger before the pump. The crude product was dissolved in diethyl ether and the phases separated. The organic layer was dried over sodium sulfate and concentrated keeping the water bath at 40° C. and the pressure at 250 mbar to give 2,2,3,3,4,4-hexadeuterocyclobutanone (5.45 g, 42%) as a pale yellow oil.

GC (Method F): 20 min, at 4.93 min, 99.03%.

To a stirred suspension of magnesium (8.70 g, 0.358 mol) and iodine (1 crystal) in diethyl ether (25 mL) under argon was added a few drops of a solution of 1,1,1-trideuteromethyl iodide in diethyl ether and the mixture was gently warmed for 1 minute until the colour dissipated. The remaining 1,1,1-trideuteromethyl iodide (8.91 mL, 0.143 mol) in diethyl ether (25 mL) was added at a rate to control the exotherm and maintain the reaction at a gentle reflux. After the addition was complete the reaction mixture was stirred at room temperature for 30 minutes then cooled to 0° C. A solution of 2,2,3,3,4,4-hexadeuterocyclobutanone (5.45 g, 0.0720 mmol) in diethyl ether (25 mL) was added slowly during which time an exotherm to reflux occurred. The reaction mixture was stirred at 0° C. for 30 minutes then at room temperature for 30 minutes. The mixture was quenched by the cautious addition of saturated aqueous ammonium chloride, diluted with water (400 mL) then diethyl ether (400 mL). The phases were separated and the aqueous phase was extracted with diethyl ether (400 mL). The combined organic layers were washed with brine, dried over sodium sulfate and carefully concentrated to give 1-(1,1,1-trideuteromethyl)-2,2,3,3,4,4-hexadeuterocyclobutanol (2.42 g, 36%).

GC (Method F): 20 min, at 5.84 min, 96.38%.

To a cooled stirred solution of 1-(1,1,1-trideuteromethyl)-2,2,3,3,4,4-hexadeuterocyclobutanol (2.42 g, 25.4 mmol) in 2-chloroacetonitrile (8.0 mL, 127 mmol) was added acetic acid-d4 (7.3 mL, 127 mmol) and sulfuric acid-d2 (4.2 mL, 76.3 mmol) and the reaction mixture was warmed slowly to room temperature and stirred for 3 hours. The mixture was added to ice and extracted with dichloromethane (2×30 mL). The combined organic layers were washed with aqueous sodium carbonate solution (30 mL), then brine, dried over sodium sulfate and concentrated to give 2-chloro-N-(1-(1,1,1-trideuteromethyl)-2,2,3,3,4,4-hexadeuterocyclobutyl) acetamide (3.95 g, 91%).

LCMS (Method D): m/z 169 (M+H)$^+$ (ES$^+$), at 1.04 min.

To a stirred solution of 2-chloro-N-(1-(1,1,1-trideuteromethyl)-2,2,3,3,4,4-hexadeuterocyclobutyl)acetamide (8.52 g, 48.2 mol) in industrial methylated spirits (50 mL) and acetic acid (10 mL) was added thiourea (7.60 g, 99.8 mmol) and the reaction mixture was heated to reflux overnight. The solid was removed by filtration and washed with industrial methylated spirits. Hydrochloric acid (10 mL, 2 M) was added to the filtrate then the industrial methylated spirits was removed under reduced pressure. The residue was partitioned between diethyl ether and water. The aqueous layer was basified to pH 10 by the addition of sodium hydroxide (2 M) and extracted with diethyl ether (3×50 mL). The combined organic layers were dried over sodium sulfate. Hydrochloric acid (4 M in dioxane) was added and the mixture stirred for 1 hour at room temperature. The mixture was concentrated and azeotroped 3 times with toluene and isopropyl alcohol to give a pale yellow solid. The solid was triturated in diethyl ether and dried in a vacuum oven to give 1-(1,1,1-trideuteromethyl)-2,2,3,3,4,4-hexadeuterocyclobutan-1-amine hydrochloride (1.29 g, 43%).

LCMS (Method E): m/z 95 (M+H)$^+$ (ES$^+$), at 0.92 min.
GC (Method G): 30 min, at 20.56 min, 90.57%.

TABLE 2

Table 2 - Starting Materials and Intermediates

| Intermediate | Name | Data |
|---|---|---|
| 1 | ethyl piperidine-4-carboxylate | Commercially available, CAS: 1126-09-6 |
| 2 | ethyl 4-fluoropiperidine-4-carboxylate hydrochloride | Commercially available, CAS: 845909-49-1 |
| 3 | methyl 4-methoxypiperidine-4-carboxylate hydrochloride | Commercially available, CAS: 1190314-13-6 |
| 4 | ethyl 3-oxo-8-azabicyclo[3.2.1]octane-8-carboxylate | Commercially available, CAS: 32499-64-2 |
| 5 | tert-butyl 3-oxo-8-azabicyclo[3.2.1]octane-8-carboxylate | Commercially available, CAS: 185099-67-6 |
| 6 | tert-butyl 3-oxo-9-azabicyclo[3.3.1]nonane-9-carboxylate | Commercially available, CAS: 512822-27-4 |
| 7 | tert-butyl 3-oxo-6-azabicyclo[3.2.1]octane-6-carboxylate | Commercially available, CAS: 359779-74-1 |
| 8 | tert-butyl 5-oxohexahydro cyclopenta[c]pyrrole-2(1H)-carboxylate | Commercially available, CAS: 148404-28-8 |
| 9 | tert-butyl 2-oxo-6-azaspiro[3.4]octane-6-carboxylate | Commercially available, CAS: 203661-71-6 |
| 10 | tert-butyl 6-oxo-2-azaspiro[3.4]octane-2-carboxylate | Commercially available, CAS: 1363382-39-1 |
| 11 | (1-methylcyclobutyl)amine hydrochloride | Commercially available, CAS: 174886-05-6 |
| 12 | tert-butylamine | Commercially available, CAS: 75-64-9 |

TABLE 2-continued

Table 2 - Starting Materials and Intermediates

| Intermediate | Name | Data |
| --- | --- | --- |
| 13 | isobutylamine | Commercially available, CAS: 78-81-9 |
| 14 | 1,1-dimethylpropylamine | Commercially available, CAS: 594-39-8 |
| 15 | cyclobutanamine | Commercially available, CAS: 2516-34-9 |
| 16 | cyclopentanamine | Commercially available, CAS: 1003-03-8 |
| 17 | cyclobutylmethylamine hydrochloride | Commercially available, CAS: 5454-82-0 |
| 18 | (1-methylcyclobutyl)methanamine hydrochloride | Commercially available, CAS: 1245647-53-3 |
| 19 | 1-(fluoromethyl)cyclobutan-1-amine hydrochloride | See experimental section |
| 20 | 1-(1,1,1-trideuteromethyl) cyclobutan-1-amine hydrochloride | See experimental section |
| 21 | 1-(1,1,1-trideuteromethyl)-2,2,3,3,4,4-hexadeuterocyclobutan-1-amine hydrochloride | See experimental section |
| 22 | 2-Fluoroethyl chloroformate | Commercially available, CAS: 462-27-1 |
| 23 | Vinyl chloroformate | Commercially available, CAS: 5130-24-5 |
| 24 | 2,2,2-Trideuteroethanol | Commercially available, CAS: 1759-87-1 |
| 25 | 1,1,2,2,2-Pentadeuteroethanol | Commercially available, CAS: 1859-08-1 |

TABLE 3

| Ex. No. | Name | Intermediate | Synthetic method | ¹H NMR | LCMS Method | LCMS data |
|---|---|---|---|---|---|---|
| 1 | Isomer 1: ethyl 3-{4-[(1-methylcyclobutyl)carbamoyl]piperidin-1-yl}-8-azabicyclo[3.2.1]octane-8-carboxylate | 1, 4 and 11 | a | (500 MHz, DMSO-d₆) δ: 1.07-1.27 (m, 4H), 1.35 (s, 3H), 1.41-1.78 (m, 10H), 1.78-2.17 (m, 7H), 2.09-2.31 (m, 3H), 2.65-3.18 (m, 2H), 3.53-3.70 (m, 1H), 4.08 (q, J = 6.9, 2H), 4.17-4.22 (m, 2H), 8.96 (br. s, 1H). | B | m/z 378 (M + H)⁺ (ES⁺), at 3.31 min, UV inactive |
| 1 | Isomer 2: ethyl 3-{4-[(1-methylcyclobutyl)carbamoyl]piperidin-1-yl}-8-azabicyclo[3.2.1]octane-8-carboxylate | 1, 4 and 11 | a | (500 MHz, DMSO-d₆) δ: 1.09-1.24 (m, 3H), 1.30-1.40 (m, 3H), 1.46-1.61 (m, 2H), 1.65-1.67 (m, 2H), 1.68-1.80 (m, 5H), 1.80-1.98 (m, 9H), 2.02-2.06 (m, 1H), 2.13-2.36 (m, 3H), 3.06-3.26 (m, 2H), 3.97-4.21 (m, 4H), 7.76 (br. s, 1H). | B | m/z 378 (M + H)⁺ (ES⁺), at 3.40 min, UV inactive |
| 2 | Isomer 1: prop-2-yn-1-yl 3-{4-[(1-methylcyclobutyl)carbamoyl]piperidin-1-yl}-8-azabicyclo[3.2.1]octane-8-carboxylate | 1, 5 and 11 | c | (400 MHz, DMSO-d₆) δ: 1.32 (s, 3H), 1.39-1.78 (m, 12H), 1.78-1.92 (m, 5H), 1.92-2.08 (m, 3H), 2.11-2.26 (m, 2H), 2.78-2.82 (m, 2H), 3.50-3.54 (m, 1H), 4.13-4.18 (m, 2H), 4.65-4.69 (m, 2H), 7.70 (br. s, 1H). | B | m/z 388 (M + H)⁺ (ES⁺), at 3.30 min, UV inactive |
| 2 | Isomer 2: prop-2-yn-1-yl 3-{4-[(1-methylcyclobutyl)carbamoyl]piperidin-1-yl}-8-azabicyclo[3.2.1]octane-8-carboxylate | 1, 5 and 11 | c | (400 MHz, DMSO-d₆) δ: 1.33 (s, 3H), 1.42-1.58 (m, 2H), 1.58-1.81 (m, 7H), 1.81-2.07 (m, 10H), 2.11-2.27 (m, 3H), 3.04-3.20 (m, 2H), 3.49-3.53 (m, 1H), 4.06-4.10 (m, 2H), 4.66-4.68 (m, 2H), 7.73 (s, 1H). | B | m/z 388 (M + H)⁺ (ES⁺), at 3.34 min, UV inactive |
| 3 | Isomer 1: but-2-yn-1-yl 3-{4-[(1-methylcyclobutyl)carbamoyl]piperidin-1-yl}-8-azabicyclo[3.2.1]octane-8-carboxylate | 1, 5 and 11 | c | (400 MHz, DMSO-d₆) δ: 1.32 (s, 3H), 1.37-1.65 (m, 7H), 1.65-1.80 (m, 5H), 1.80-1.91 (m, 7H), 1.91-2.09 (m, 4H), 2.11-2.27 (m, 2H), 2.80-2.84 (m, 3H), 4.38-4.42 (m, 1H), 4.57-4.61 (m, 2H), 7.70 (br. s, 1H). | B | m/z 402 (M + H)⁺ (ES⁺), at 3.28 min, UV inactive |
| 3 | Isomer 2: but-2-yn-1-yl 3-{4-[(1-methylcyclobutyl)carbamoyl]piperidin-1-yl}-8-azabicyclo[3.2.1]octane-8-carboxylate | 1, 5 and 11 | c | (400 MHz, DMSO-d₆) δ: 1.32 (s, 3H), 1.38-1.53 (m, 3H), 1.53-1.68 (m, 6H), 1.68-1.78 (m, 3H), 1.78-1.92 (m, 7H), 1.97-2.00 (m, 3H), 2.11-2.24 (m, 2H), 2.75-2.81 (m, 3H), 4.12-4.16 (m, 2H), 4.61-4.67 (m, 2H), 7.70 (br. s, 1H). | B | m/z 402 (M + H)⁺ (ES⁺), at 3.54 min, UV inactive |
| 4 | ethyl 3-{4-fluoro-4-[(1-methylcyclobutyl)carbamoyl]piperidin-1-yl}-8-azabicyclo[3.2.1]octane-8-carboxylate | 2, 4 and 11 | b | (400 MHz, DMSO-d₆) δ: 1.18 (t, J = 7.0, 3H) 1.35 (s, 3H), 1.45-1.50 (m, 2H), 1.58-1.79 (m, 8H), 1.79-2.05 (m, 6H), 2.13-2.36 (m, 4H), 2.71 (d, J = 10.3, 2H), 2.82 (dt, J = 11.0, 5.7, 1H), 4.04 (q, J = 7.0, 2H), 4.12-4.18 (m, 2H), 7.93 (br. s, 1H). | B | m/z 396 (M + H)⁺ (ES⁺), at 3.84 min, UV inactive |
| 5 | Isomer 1: ethyl 3-{4-methoxy-4-[(1-methylcyclobutyl)carbamoyl]piperidin-1-yl}-8-azabicyclo[3.2.1]octane-8-carboxylate | 3, 5 and 11 | b | (400 MHz, DMSO-d₆) δ: 1.17 (t, J = 7.0, 3H), 1.34 (s, 3H), 1.37-1.54 (m, 2H), 1.67-1.79 (m, 11H), 1.79-1.95 (m, 4H), 2.12-2.31 (m, 4H), 2.51-2.54 (m, 1H), 2.70-2.73 (m, 1H), 3.06 (s, 3H), 4.04 (q, J = 7.0, 2H), 4.12-4.16 (m, 2H), 7.65 (br. s, 1H). | B | m/z 408 (M + H)⁺ (ES⁺), at 3.52 min, UV inactive |
| 6 | Mixture of diastereomers: ethyl 3-{4-[(1-methylcyclobutyl)carbamoyl]piperidin-1-yl}-9-azabicyclo[3.3.1]nonane-9-carboxylate | 1, 6 and 11 | c | (400 MHz, DMSO-d₆) δ: 1.17 t, J = 7.0, 3H), 1.32 (s, 3H), 1.47-1.53 (m, 5H), 1.55-1.68 (m, 6H), 1.70-1.86 (m, 7H), 1.95-2.01 (m, 3H), 2.11-2.24 (m, 2H), 2.86-2.90 (m, 2H), 3.08-3.12 (m, 1H), 4.03 (q, J = 7.0, 2H), 4.19-4.24 (m, 2H), 7.71 (br. s, 1H). | A | m/z 392 (M + H)⁺ (ES⁺), at 1.67 min, UV inactive |

TABLE 3-continued

| Ex. No. | Name | Intermediate | Synthetic method | $^1$H NMR | LCMS Method | LCMS data |
|---|---|---|---|---|---|---|
| 7 | Mixture of diastereomers: ethyl 3-[4-[(1-methylcyclobutyl)carbamoyl]piperidin-1-yl]-6-azabicyclo[3.2.1]octane-6-carboxylate | 1, 7 and 11 | c | (400 MHz, DMSO-d$_6$) δ: 1.15-1.21 (m, 3H), 1.33 (s, 3H), 1.38-1.59 (m, 3H), 1.59-1.79 (m, 7H), 1.79-2.08 (m, 6H), 2.11-2.27 (m, 3H), 2.27-2.46 (m, 2H), 3.02-3.18 (m, 4H), 3.86-4.15 (m, 3H), 7.78 (br. s, 1H). | B | m/z 378 (M + H)$^+$ (ES$^+$), at 3.14 and 3.28 min, UV inactive |
| 8 | Mixture of diastereomers: ethyl 5-{4-[(1-methylcyclobutyl)carbamoyl]piperidin-1-yl}-hexahydrocyclopenta[c]pyrrole-2(1H)-carboxylate | 1, 8 and 11 | c | (400 MHz, DMSO-d$_6$) δ: 1.16-1.21 (m, 5H), 1.30-1.42 (m, 3H), 1.59-1.81 (m, 5H), 1.81-1.97 (m, 5H), 2.14-2.35 (m, 5H), 2.57-2.61 (m, 2H), 2.77-2.89 (m, 1 H), 3.03-3.13 (m, 2H), 3.40-3.53 (m, 4H), 4.02 (q, J = 7.0, 2H), 7.93-7.99 (m, 1H). | B | m/z 378 (M + H)$^+$ (ES$^+$), at 3.37 min, UV inactive |
| 9 | Mixture of diastereomers: ethyl 2-{4-[(1-methylcyclobutyl)carbamoyl]piperidin-1-yl}-6-azaspiro[3.4]octane-6-carboxylate | 1, 9 and 11 | c | (400 MHz, DMSO-d$_6$) δ: 1.10-1.21 (m, 3H), 1.32 (s, 3H), 1.40-1.54 (m, 2H), 1.57-1.61 (m, 4H), 1.68-1.90 (m, 8H), 1.90-2.08 (m, 3H), 2.11-2.26 (m, 2H), 2.55-2.72 (m, 1H), 2.75-2.79 (m, 2H), 3.09-3.28 (m, 4H), 3.88-4.09 (m, 2H), 7.73 (s, 1H). | B | m/z 378 (M + H)$^+$ (ES$^+$), at 3.31 and 3.45 min, UV inactive |
| 9 | Isomer 1: ethyl 2-{4-[(1-methylcyclobutyl)carbamoyl]piperidin-1-yl}-6-azaspiro[3.4]octane-6-carboxylate | 1, 9 and 11 | d | (400 MHz, CDCl$_3$) δ: 1.20-1.31 (m, 3H), 1.45 (s, 3H), 1.72-1.96 (m, 9H), 1.97-2.18 (m, 8H), 2.18-2.30 (m, 2H), 2.50-2.60 (m, 1H), 2.89-3.01 (m, 2H), 3.23-3.44 (m, 4H), 4.14 (q, J = 7.0 Hz, 2H), 5.51 (br. s, 1H). | B | m/z 378 (M + H)$^+$ (ES$^+$), at 3.31 min, UV inactive |
| 9 | Isomer 2: ethyl 2-{4-[(1-methylcyclobutyl)carbamoyl]piperidin-1-yl}-6-azaspiro[3.4]octane-6-carboxylate | 1, 9 and 11 | d | (400 MHz, CDCl$_3$) δ: 1.20-1.29 (m, 3H), 1.45 (s, 3H), 1.68-1.97 (m, 9H), 1.97-2.18 (m, 8H), 2.19-2.29 (m, 2H), 2.77-2.95 (m, 1H), 2.96-3.06 (m, 2H), 3.26-3.34 (m, 2H), 3.34-3.46 (m, 2H), 4.10 (q, J = 7.0, 2H), 5.75 (br. s, 1H). | B | m/z 378 (M + H)$^+$ (ES$^+$), at 3.45 min, UV inactive |
| 10 | Mixture of diastereomers: but-2-yn-1-yl 2-{4-[(1-methylcyclobutyl)carbamoyl]piperidin-1-yl}-6-azaspiro[3.4]octane-6-carboxylate | 1, 9 and 11 | c | (400 MHz, DMSO-d$_6$) δ: 1.33 (s, 3H), 1.42-1.67 (m, 6H), 1.71-1.88 (m, 11H), 1.92-2.05 (m, 3H), 2.17-2.23 (m, 2H), 2.62-2.82 (m, 2H), 3.22-3.31 (m, 4H), 4.59-4.62 (m, 2H), 7.72 (br. s, 1H). | B | m/z 402 (M + H)$^+$ (ES$^+$), at 3.57 and 3.67 min, UV inactive |
| 11 | Mixture of diastereomers: ethyl 2-{4-fluoro-4-[(1-methylcyclobutyl)carbamoyl]piperidin-1-yl}-6-azaspiro[3.4]octane-6-carboxylate | 2, 9 and 11 | e | (400 MHz, DMSO-d$_6$) δ: 1.17 (t, J = 7.2, 3H), 1.36 (s, 3H), 1.67-1.85 (m, 8H), 1.85-1.96 (m, 5H), 1.97-2.04 (m, 3H), 2.12-2.30 (m, 2H), 2.65-2.70 (m, 3H), 3.07-3.30 (m, 4H), 3.87-4.10 (m, 2H), 7.93 (br. s, 1H). | B | m/z 396 (M + H)$^+$ (ES$^+$), at 3.77 and 3.90 min, UV inactive |
| 12 | Racemic: ethyl 6-{4-[(1-methylcyclobutyl)carbamoyl]piperidin-1-yl}-2-azaspiro[3.4]octane-2-carboxylate | 1, 10 and 11 | c | (400 MHz, DMSO-d$_6$) δ: 1.15 (t, J = 7.0, 3H), 1.33 (s, 3H), 1.40-1.65 (m, 6H), 1.71-1.87 (m, 10H), 1.95-2.05 (m, 2H), 2.15-2.23 (m, 2H), 2.80-2.92 (m, 2H), 3.67-3.80 (m, 4H), 3.98 (q, J = 7.0, 2H), 7.69 (br. s, 1H). | B | m/z 378 (M + H)$^+$ (ES$^+$), at 3.34 min, UV inactive |
| 13 | Racemic: prop-2-yn-1-yl 6-{4-[(1-methylcyclobutyl)carbamoyl]piperidin-1-yl}-2-azaspiro[3.4]octane-2-carboxylate | 1, 10 and 11 | c | (400 MHz, DMSO-d$_6$) δ: 1.33 (s, 3H), 1.42-1.88 (m, 15H), 2.08-2.23 (m, 4H), 2.90-3.04 (m, 2H), 3.50-3.51 (m, 1H), 3.71-3.84 (m, 4H), 4.61-4.63 (m, 2H), 7.76 (br. s, 1H). | B | m/z 388 (M + H)$^+$ (ES$^+$), at 3.31 min, UV inactive |
| 14 | Mixture of diastereomers: ethyl 2-[4-(tert-butylcarbamoyl)piperidin-1-yl]-6-azaspiro[3.4]octane-6-carboxylate | 1, 9 and 12 | f | (400 MHz, CDCl$_3$) δ: 1.21-1.27 (m, 3H), 1.33 (s, 9H), 1.75-2.25 (m, 13H), 2.65-2.80 (m, 1H), 2.90-3.02 (m, 2H), 3.25-3.45 (m, 4H), 4.05-4.16 (J = 7.0, 2H), 5.30 (br. s, 1H). | B | m/z 366 (M + H)$^+$ (ES$^+$), at 3.28 and 3.42 min, UV inactive |

TABLE 3-continued

| Ex. No. | Name | Intermediate | Synthetic method | $^1$H NMR | LCMS Method | LCMS data |
|---|---|---|---|---|---|---|
| 15 | Mixture of diastereomers: ethyl 2-{4-[(2-methylpropyl)carbamoyl]piperidin-1-yl}-6-azaspiro[3.4]octane-6-carboxylate | 1, 9 and 13 | g | (400 MHz, CDCl$_3$) δ: 0.90 (d, J = 6.5 Hz, 6H), 1.22-1.29 (m, 3H), 1.72-1.98 (m, 10H), 2.01-2.20 (m, 4H), 2.63-2.75 (m, 1H), 2.89-2.99 (m, 2H), 3.08 (t, J = 6.5 Hz, 2H), 3.22-3.45 (m, 4H), 4.08-4.15 (m, 2H), 5.51 (br. s, 1H). | B | m/z 366 (M + H)$^+$ (ES$^+$), at 3.10 and 3.16 min, UV inactive |
| 16 | Mixture of diastereomers: ethyl 2-{4-[(2-methylbutan-2-yl)carbamoyl]piperidin-1-yl}-6-azaspiro[3.4]octane-6-carboxylate | 1, 9 and 14 | g | (400 MHz, CDCl$_3$) δ: 0.82 (t, J = 7.5 Hz, 3H), 1.19-1.32 (m, 9H), 1.45 (m, 1H), 1.71 (q, J = 7.5 Hz, 2H), 1.77-2.00 (m, 6H), 2.01-2.30 (m, 6H), 2.93-3.11 (m, 3H), 3.26-3.44 (m, 4H), 4.08-4.15 (m, 2H), 5.36 (br. s, 1H). | B | m/z 380 (M + H)$^+$ (ES$^+$), at 3.54 and 3.67 min, UV inactive |
| 17 | Mixture of diastereomers: ethyl 2-[4-(cyclobutylcarbamoyl)piperidin-1-yl]-6-azaspiro[3.4]octane-6-carboxylate | 1, 9 and 15 | g | (400 MHz, CDCl$_3$) δ: 1.16-1.31 (m, 3H), 1.40-1.49 (m, 1H), 1.64-1.99 (m, 9H), 2.00-2.09 (m, 2H), 2.10-2.25 (m, 5H), 2.25-2.42 (m, 1H), 2.89-3.12 (m, 3H), 3.29-3.47 (m, 3H), 4.18-4.15 (m, 2H), 4.26-4.40 (m, 1H), 5.98 (br. s, 1 H). | B | m/z 364 (M + H)$^+$ (ES$^+$), at 2.96 and 3.13 min, UV inactive |
| 18 | Mixture of diastereomers: ethyl 2-[4-(cyclopentylcarbamoyl)piperidin-1-yl]-6-azaspiro[3.4]octane-6-carboxylate | 1, 9 and 16 | g | (400 MHz, CDCl$_3$) δ: 1.22-1.29 (m, 3H), 1.31-1.37 (m, 2H), 1.70-1.81 (m, 3H), 1.81-2.06 (m, 12H), 2.06-2.36 (m, 4H), 2.74-2.89 (m, 1H), 2.91-3.03 (m, 2H), 3.19-3.45 (m, 4H), 4.02-4.28 (m, 3H), 5.53 (br. s, 1H). | B | m/z 378 (M + H)$^+$ (ES$^+$), at 3.23 and 3.35 min, UV inactive |
| 19 | Mixture of diastereomers: ethyl 2-{4-[(cyclobutylmethyl)carbamoyl]piperidin-1-yl}-6-azaspiro[3.4]octane-6-carboxylate | 1, 9 and 17 | g | (400 MHz, CDCl$_3$) δ: 1.21-1.29 (m, 3H), 1.40-1.50 (m, 1H), 1.60-1.72 (m, 2H), 1.75-2.37 (m, 16H), 2.37-2.51 (m, 1H), 2.89-3.15 (m, 3H), 3.22-3.28 (m, 2H), 3.29-3.44 (m, 4H), 4.08-4.15 (m, 2H), 5.73 (br. s, 1H). | B | m/z 378 (M + H)$^+$ (ES$^+$), at 3.31 and 3.46 min, UV inactive |
| 20 | Mixture of diastereomers: ethyl 2-{4-{[(1-methylcyclobutyl)methyl]carbamoyl}piperidin-1-yl}-6-azaspiro[3.4]octane-6-carboxylate | 1, 9 and 18 | g | (400 MHz, CDCl$_3$) δ: 1.10 (s, 3H), 1.21-1.28 (m, 3H), 1.49-1.57 (m, 1H), 1.65-1.72 (m, 2H), 1.79-2.48 (m, 16H), 2.75-2.85 (m, 1H), 3.08-3.27 (m, 4H), 3.30-3.46 (m, 4H), 4.07-4.15 (m, 2H), 6.05 (br. s, 1H). | B | m/z 392 (M + H)$^+$ (ES$^+$), at 3.61 and 3.73 min, UV inactive |
| 21 | Isomer 2: ethyl 2-(4-{[1-(1,1,1-trideuteromethyl)cyclobutyl]carbamoyl}piperidin-1-yl)-6-azaspiro[3.4]octane-6-carboxylate | 1, 9 and 20 | d | (400 MHz, CDCl$_3$) δ: 1.21-1.35 (m, 3H), 1.51-2.39 (m, 19H), 2.62-2.76 (m, 1H), 2.79-3.04 (m, 2H), 3.22-3.51 (m, 4H), 4.08-4.20 (m, 2H), 5.49 (br. s, 1H). | B | m/z 381 (M + H)$^+$ (ES$^+$), at 3.45 min, UV inactive |
| 22 | Isomer 2: ethyl 2-(4-{[1-(1,1,1-trideuteromethyl)-2,2,3,3,4,4-hexadeuterocyclobutyl]carbamoyl}piperidin-1-yl)-6-azaspiro[3.4]octane-6-carboxylate | 1, 9 and 21 | d | (400 MHz, CDCl$_3$) δ: 1.24 (t, J = 7.0, 3H), 1.56-2.17 (m, 12H), 2.58-2.81 (m, 1H), 2.81-3.00 (m, 2H), 3.18-3.49 (m, 4H), 4.10 (q, J = 7.0, 2H), 5.54 (br. s, 1H). | C | m/z 387 (M + H)$^+$ (ES$^+$), at 3.84 min, UV inactive |
| 23 | Isomer 2: ethyl 2-(4-{[1-(fluoromethyl)cyclobutyl]carbamoyl}piperidin-1-yl)-6-azaspiro[3.4]octane-6-carboxylate | 1, 9 and 19 | d | (400 MHz, CDCl$_3$) δ: 1.21-1.35 (m, 3H), 1.50-1.74 (m, 7H), 1.74-1.93 (m, 5H), 1.93-2.08 (m, 3H), 2.09 (m, 7 H), 2.34-3.55 (m, 4H), 4.06-4.17 (q, J = 7.16, 2H), 4.58 (d, J = 48, 2H), exchangeable NH not observed. | C | m/z 396 (M + H)$^+$ (ES$^+$), at 3.79 min, UV inactive |
| 24 | Mixture of diastereomers: 2-fluoroethyl 2-{4-[(1-methylcyclobutyl)carbamoyl]piperidin-1-yl}-6-azaspiro[3.4]octane-6-carboxylate | 1, 9, 11 and 22 | c | (400 MHz, CDCl$_3$) δ: 1.44 (s, 3H), 1.66-2.15 (m, 17H), 2.19-2.29 (m, 2H), 2.54-2.81 (m, 1H), 2.81-2.99 (m, 2H), 3.27-3.33 (m, 1H), 3.34-3.48 (m, 3H), 4.23-4.31 (m, 1H), 4.33-4.40 (m, 1H), 4.50-4.58 (m, 1H), 4.62-4.70 (m, 1H), 5.51 (br. s, 1H). | B | m/z 396 (M + H)$^+$ (ES$^+$), at 3.11 and 3.33 min, UV inactive |
| 25 | Isomer 2: (2,2,2-trideutero)ethyl 2-{4-[(1-methylcyclobutyl)carbamoyl]piperidin-1-yl}-6-azaspiro[3.4]octane-6-carboxylate | 1, 9, 11 and 24 | h | 400 MHz, CDCl$_3$) δ: 1.45 (s, 3H), 1.54-2.33 (m, 18 H), 2.33-3.46 (m, 8H), 4.12 (s, 2H), 5.37-6.23 (m, 1H). | C | m/z 381 (M + H)$^+$ (ES$^+$), at 3.92 min, UV inactive |

TABLE 3-continued

| Ex. No. | Name | Intermediate | Synthetic method | ¹H NMR | LCMS Method | LCMS data |
|---|---|---|---|---|---|---|
| 26 | Isomer 2: (2,2,2-trideutero)ethyl 2-(4-{[1-(1,1,1-trideuteromethyl)cyclobutyl]carbamoyl}piperidin-1-yl)-6-azaspiro[3.4]octane-6-carboxylate | 1, 9, 20 and 24 | h | 400 MHz, CDCl₃) δ: 1.65-1.91 (m, 10H), 1.91-2.09 (m, 7H), 2.11-2.33 (m, 2H), 2.58-2.81 (m, 1H), 2.82-2.99 (m, 2 H), 3.17-3.32 (m, 2H), 3.32-3.50 (m, 2H), 4.09 (s, 2H), 5.56 (br. s, 1H). | C | m/z 384 (M + H)⁺ (ES⁺), at 3.99 min, UV inactive |
| 27 | Mixture of diastereomers: (2,2,2-trideutero)ethyl 2-(4-{[1-(1,1,1-trideuteromethyl)-2,2,3,4,4-hexadeuterocyclobutyl]carbamoyl}piperidin-1-yl)-6-azaspiro[3.4]octane-6-carboxylate | 1, 9, 21 and 24 | h | 400 MHz, CDCl₃) δ: 1.48-2.50 (m, 13 H), 2.61-3.08 (m, 3H), 3.18-3.53 (m, 4H), 4.10 (s, 2H), 5.60 (br. s, 1H). | C | m/z 390 (M + H)⁺ (ES⁺), at 3.70 and 3.84 min, UV inactive |
| 27 | Isomer 2: (2,2,2-trideutero)ethyl 2-(4-{[1-(1,1,1-trideuteromethyl)-2,2,3,4,4-hexadeuterocyclobutyl]carbamoyl}piperidin-1-yl)-6-azaspiro[3.4]octane-6-carboxylate | 1, 9, 21 and 24 | h | 400 MHz, CDCl₃) δ: 1.49-2.38 (m, 13 H), 2.98-3.28 (m, 3H), 3.30-3.50 (m, 4H), 4.08 (s, 2H), 6.03 (br. s, 1H). | C | m/z 390 (M + H)⁺ (ES⁺), at 3.84 min, UV inactive |
| 28 | Isomer 2: (2,2,2-trideutero)ethyl 2-(4-{[1-(fluoromethyl)cyclobutyl]carbamoyl}piperidin-1-yl)-6-azaspiro[3.4]octane-6-carboxylate | 1, 9, 19 and 24 | h | (400 MHz, CDCl₃) δ: 1.52-2.29 (m, 19H), 2.56-2.81 (m, 1 H), 2.82-3.06 (m, 2H), 3.17-3.51 (m, 4H), 4.10 (s, 2H), 4.58 (d, J = 48, 2H), 5.67 (br. s, 1H). | C | m/z 399 (M + H)⁺ (ES⁺), at 3.73 min, UV inactive |
| 29 | Isomer 2: (1,1,2,2,2-pentadeutero)ethyl 2-{4-[(1-methylcyclobutyl)carbamoyl]piperidin-1-yl}-6-azaspiro[3.4]octane-6-carboxylate | 1, 9, 11 and 25 | h | 400 MHz, CDCl₃) δ: 1.45 (s, 3H), 1.52-2.33 (m, 18 H), 2.36-3.57 (m, 8H), 5.37-6.23 (m, 1H). | C | m/z 383 (M + H)⁺ (ES⁺), at 3.92 min, UV inactive |
| 30 | Isomer 2: (1,1,2,2,2-pentadeutero)ethyl 2-(4-{[1-(1,1,1-trideuteromethyl)cyclobutyl]carbamoyl}piperidin-1-yl)-6-azaspiro[3.4]octane-6-carboxylate | 1, 9, 20 and 25 | h | 400 MHz, CDCl₃) δ: 1.67-1.94 (m, 12H), 1.96-2.06 (m, 5H), 2.10-2.32 (m, 2H), 2.59-2.74 (m, 1H), 2.82-2.94 (m, 2 H), 3.21-3.31 (m, 2H), 3.31-3.48 (m, 2H), 5.55 (br. s, 1H). | C | m/z 386 (M + H)⁺ (ES⁺), at 3.93 min, UV inactive |
| 31 | Isomer 2: (1,1,2,2,2-pentadeutero)ethyl 2-(4-{[1-(1,1,1-trideuteromethyl)-2,2,3,4,4-hexadeuterocyclobutyl]carbamoyl}piperidin-1-yl)-6-azaspiro[3.4]octane-6-carboxylate | 1, 9, 21 and 25 | h | 400 MHz, CDCl₃) δ: 1.60-2.34 (m, 13 H), 2.63-3.60 (m, 7H), 5.79 (br. s, 1H). | C | m/z 392 (M + H)⁺ (ES⁺), at 3.73 and 3.82 min, UV inactive |
| 31 | Isomer 2: (1,1,2,2,2-pentadeutero)ethyl 2-(4-{[1-(1,1,1-trideuteromethyl)-2,2,3,4,4-hexadeuterocyclobutyl]carbamoyl}piperidin-1-yl)-6-azaspiro[3.4]octane-6-carboxylate | 1, 9, 21 and 25 | h | 400 MHz, CDCl₃) δ: 1.44-2.33 (m, 13 H), 2.37-3.12 (m, 3H), 3.14-3.53 (m, 4H), 5.56 (br. s, 1H). | C | m/z 392 (M + H)⁺ (ES⁺), at 3.81 min, UV inactive |
| 32 | Mixture of diastereomers: ethenyl 2-{4-[(1-methylcyclobutyl)carbamoyl]piperidin-1-yl}-6-azaspiro[3.4]octane-6-carboxylate | 1, 9, 11 and 23 | c | (400 MHz, CDCl₃) δ: 1.43 (s, 3H), 1.59-2.15 (m, 17H), 2.17-2.30 (m, 2H), 2.56-2.73 (m, 1H), 2.77-2.97 (m, 2H), 3.27-3.54 (m, 4H), 4.41 (ddd, J = 15.0, 5.0 and 1.3 Hz, 1H), 4.67-4.84 (m, 1H), 5.56 (br. s, 1H), 7.15-7.26 (m, 1H). | B | m/z 376 (M + H)⁺ (ES⁺), at 3.43 and 3.51 min, UV inactive |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen*, 2008). ERK1/2 phosphorylation is a downstream consequence of both Gq/11 and Gi/o protein coupled receptor activation, making it highly suitable for the assessment of M1, M3 (Gq/11 coupled) and M2, M4 receptors (Gi/o coupled), rather than using different assay formats for different receptor subtypes. CHO cells stably expressing the human muscarinic M1, M2, M3 or M4 receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader.

$pEC_{50}$ and $E_{max}$ figures were calculated from the resulting data for each receptor subtype.

The results are set out in Table 4 below.

TABLE 4

| | Muscarinic Activity | | | |
|---|---|---|---|---|
| Ex. No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| ACh | 8.33 (102) | 7.82 (105) | 812 (115) | 8.09 (110) |
| 1 - Isomer 1 | 6.49 (99) | NT | NT | 5.99 (51) |
| 1 - Isomer 2 | 7.38 (102) | <4.7 (0) | <4.7 (18) | 6.77 (98) |
| 2 - Isomer 1 | 6.48 (94) | <4.7 (14) | <4.7 (7) | <4.7 (11) |
| 3 - Isomer 2 | 6.44 (109) | <4.7 (10) | <4.7 (2) | 6.07 (65) |
| 4 - Isomer 2 | 6.84 (111) | NT | NT | 5.97 (44) |
| 6 - mixture of diastereomers | 7.36 (151) | <4.7 (13) | <4.7 (5) | 6.33 (54) |
| 7 - mixture of diastereomers | 7.26 (127) | <4.7 (10) | <4.7 (4) | 6.35 (81) |
| 8 - mixture of diastereomers | 6.96 (118) | <4.7 (5) | <4.7 (8) | 5.77 (29) |
| 9 - mixture of diastereomers | 7.29 (142) | <4.7 (6) | <4.7 (5) | 6.42 (66) |
| 9 - Isomer 1 | 6.52 (102) | NT | NT | 6.23 (67) |
| 9 - Isomer 2 | 7.44 (100) | <4.7 (15) | <4.7 (9) | 6.74 (66) |
| 10 - mixture of diastereomers | 6.81 (93) | <4.7 (10) | <4.7 (3) | 6.47 (42) |
| 11 - mixture of diastereomers | 7.55 (112) | <4.7 (6) | <4.7 (4) | 6.69 (77) |
| 12 - racemic | 7.45 (141) | <4.7 (8) | <4.7 (78) | 7.27 (49) |
| 13 - racemic | 7.80 (139) | <4.7 (7) | <4.7 (39) | 7.28 (44) |
| 16 - mixture of diastereomers | 6.51 (113) | NT | NT | 6.19 (56) |
| 18 - mixture of diastereomers | 6.58 (100) | NT | NT | 6.17 (67) |
| 19 - mixture of diastereomers | 6.44 (109) | NT | NT | 5.99 (42) |
| 21 - Isomer 2 | 7.17 (107) | <4.7 (9) | <4.7 (12) | 6.77 (111) |
| 22 - Isomer 2 | 7.10 (103) | NT | NT | 6.68 (67) |
| 23 - Isomer 2 | 6.81 (90) | NT | NT | 6.66 (67) |
| 25 - Isomer 2 | 7.27 (108) | <4.7 (23) | <4.7 (17) | 6.76 (83) |
| 26 - Isomer 2 | 7.09 (108) | NT | NT | 6.59 (110) |
| 28 - Isomer 2 | 6.49 (120) | NT | NT | 6.51 (106) |
| 29 - Isomer 2 | 7,26 (107) | <4.7 (18) | <4.7 (13) | 6.73 (91) |
| 30 - Isomer 2 | 7.07 (105) | NT | NT | 6.71 (111) |
| 31 - mixture of diastereomers | 6.39 (110) | NT | NT | 6.19 (77) |

NT—Not tested

Example B

Passive Avoidance

Studies were carried out as described previously by Foley et al., (2004) *Neuropsychopharmacology*. In the passive avoidance task scopolamine administration (1 mg/kg, i.p.) at 6 hours following training rendered animals amnesic of the paradigm. A dose range of 3, 10, and 30 mg/kg (po) free base, administered 90 minutes prior to the training period via oral gavage, was examined.

Example 9 Isomer 2 was found to reverse scopolamine-induced amnesia of the paradigm in a dose-dependent manner, with an approximate $ED_{50}$ of ca. 10 mg/kg (po). The effect of 30 mg/kg was similar to that produced by the cholinesterase inhibitor donepezil (0.1 mg/kg, ip) which served as a positive control (FIG. 1).

Example C

CA1 Cell Firing

Rat hippocampal slices of 400 μm thickness were cut in chilled (<4° C.) artificial cerebrospinal fluid (aCSF, composition in mM: NaCl 127, KCl 1.6, $KH_2PO_4$ 1.24, $MgSO_4$ 1.3, $CaCl_2$ 2.4, $NaHCO_3$ 26 and D-glucose 10) using vibratome. Slices were maintained in oxygenated (95% $O_2$/5% $CO_2$) aCSF at room temperature for at least 1 hr prior to electrophysiological recording, after which they were transferred to an interface chamber and constantly perfused with warmed (30° C.) oxygenated aCSF at a flow rate of 1.5-3 ml·min-1. Schaffer collaterals were then stimulated (1-20 V, 0.1 ms pulse width, 0.033 Hz) with a concentric bipolar electrode to evoke field excitatory post synaptic potentials (fEPSPs) recorded from the stratum radiatum of the CA1 region. Experiments were performed to examine the effect of compound compared to 1 μM carbachol (CCh), on the amplitude of fEPSPs in the CA1 region of rat hippocampal slices. 1 μM CCh was initially applied until steady-state, followed by wash, before performing a five point cumulative concentration-response to compound. Each compound was tested on 6 slices and results averaged. Drug preparation; compound was dissolved in 100% DMSO at a stock concentration of 30 mM, and diluted according to requirements, carbamoylcholine chloride (CCh) was purchased from Sigma (Cat #C4382) and dissolved at a stock concentration of 1 mM in $ddH_2O$.

TABLE 5

| Ex. No. | Cell Firing EC50 (μM) |
|---|---|
| 9 - Isomer 2 | 5.7 |

Example D

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and optionally 1% by weight of magnesium stearate and filling the resulting mixture into standard opaque hard gelatin capsules.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula:

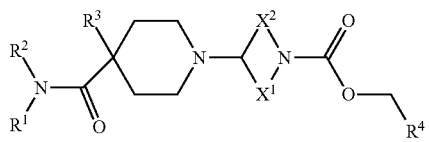

or a pharmaceutically acceptable salt thereof, wherein:
$X^1$ and $X^2$ are saturated hydrocarbon groups which together contain a total of five to nine carbon atoms and which link together such that the moiety:

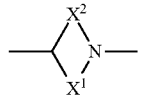

forms a bicyclic ring system selected from the group consisting of ring systems BA, BB, CA, and CB below:

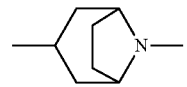
BA

BB

CA

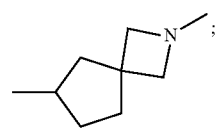
CB $R^1$ is selected from 2-methylpropyl; 2,2-dimethylpropyl; tert-butyl; 2-methyl-but-2-yl; 2,3-dimethylbut-2-yl; cyclopropylmethyl; cyclobutylmethyl; cyclopentyl; cyclopentylmethyl; 1-methylcyclobutyl; 1-methylcyclopentyl; 1-methylcyclohexyl; 1-methylcyclopentylmethyl; cyclopropyl-prop-2-yl; 1-methylcyclobutylmethyl and 1-ethyl-cyclobutylmethyl groups;

$R^2$ is selected from hydrogen, methyl, ethyl and isopropyl;
$R^3$ is selected from hydrogen, fluorine and methoxy; and
$R^4$ is a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof.

2. The compound according to claim 1 wherein $R^1$ is 1-methylcyclobutyl.

3. The compound according to claim 1 wherein $R^2$ is hydrogen.

4. The compound according to claim 1 wherein $R^3$ is hydrogen.

5. The compound according to claim 1 wherein $R^4$ is selected from methyl, fluoromethyl, ethyl, ethynyl and 1-propynyl.

6. The compound according to claim 1 wherein the moiety

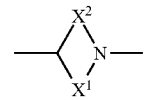

represents ring system CA:

CA

7. The compound according to claim 1, wherein the compound is ethyl 3-{4-[(1-methylcyclobutyl)carbamoyl]piperidin-1-yl}-8-azabicyclo[3.2.1]octane-8-carboxylate or a pharmaceutically acceptable salt thereof.

8. The compound according to claim 1, wherein the compound is ethyl 3-{4-[(1-methylcyclobutyl)carbamoyl]piperidin-1-yl}-9-azabicyclo[3.3.1]nonane-9-carboxylate or a pharmaceutically acceptable salt thereof.

9. The compound according to claim 1, wherein the compound is ethyl 2-{4-fluoro-4-[(1-methylcyclobutyl)carbamoyl]piperidin-1-yl}-6-azaspiro[3.4]octane-6-carboxylate or a pharmaceutically acceptable salt thereof.

10. The compound according to claim 1, wherein the compound is ethyl 6-{4-[(1-methylcyclobutyl)carbamoyl]piperidin-1-yl}-2-azaspiro[3.4]octane-2-carboxylate or a pharmaceutically acceptable salt thereof.

11. The compound according to claim 1, wherein the compound is prop-2-yn-1-yl 6-{4-[(1-methylcyclobutyl)carbamoyl]piperidin-1-yl}-2-azaspiro[3.4]octane-2-carboxylate or a pharmaceutically acceptable salt thereof.

12. The compound according to claim 1, wherein the compound is ethyl 2-{4-[(1-methylcyclobutyl)carbamoyl]piperidin-1-yl}-6-azaspiro[3.4]octane-6-carboxylate or a pharmaceutically acceptable salt thereof.

13. The compound according to claim 1, wherein the compound is ethyl 2-(4-{[1-(1,1,1-trideuteromethyl)cyclobutyl]carbamoyl}piperidin-1-yl)-6-azaspiro[3.4]octane-6-carboxylate or a pharmaceutically acceptable salt thereof.

14. The compound according to claim 1, wherein the compound is ethyl 2-(4-{[1-(1,1,1-trideuteromethyl)-2,2,3,3,4,4-hexadeuterocyclobutyl]carbamoyl}piperidin-1-yl)-6-azaspiro[3.4]octane-6-carboxylate or a pharmaceutically acceptable salt thereof.

15. The compound according to claim 1, wherein the compound is (2,2,2-trideutero)ethyl 2-{4-[(1-methylcyclobutyl)carbamoyl]piperidin-1-yl}-6-azaspiro[3.4]octane-6-carboxylate or a pharmaceutically acceptable salt thereof.

16. The compound according to claim 1, wherein the compound is (2,2,2-trideutero)ethyl 2-(4-{[1-(1,1,1-trideuteromethyl)cyclobutyl]carbamoyl}piperidin-1-yl)-6-azaspiro[3.4]octane-6-carboxylate or a pharmaceutically acceptable salt thereof.

17. The compound according to claim 1, wherein the compound is (2,2,2-trideutero)ethyl 2-(4-{[1-(1,1,1-trideuteromethyl)-2,2,3,3,4,4-hexadeuterocyclobutyl]carbamoyl}piperidin-1-yl)-6-azaspiro[3.4]octane-6-carboxylate or a pharmaceutically acceptable salt thereof.

18. The compound according to claim 1, wherein the compound is (1,1,2,2,2-pentadeutero) ethyl 2-{4-[(1-methylcyclobutyl)carbamoyl]piperidin-1-yl}-6-azaspiro[3.4]octane-6-carboxylate or a pharmaceutically acceptable salt thereof.

19. The compound according to claim 1, wherein the compound is (1,1,2,2,2-pentadeutero)ethyl 2-(4-{[1-(1,1,1-trideuteromethyl)cyclobutyl]carbamoyl}piperidin-1-yl)-6-azaspiro[3.4]octane-6-carboxylate or a pharmaceutically acceptable salt thereof.

20. The compound according to claim 1, wherein the compound is (1,1,2,2,2-pentadeutero)ethyl 2-(4-{[1-(1,1,1-trideuteromethyl)-2,2,3,3,4,4-hexadeuterocyclobutyl]carbamoyl}piperidin-1-yl)-6-azaspiro[3.4]octane-6-carboxylate or a pharmaceutically acceptable salt thereof.

* * * * *